United States Patent [19]

Szucs et al.

[11] Patent Number: 4,898,609

[45] Date of Patent: Feb. 6, 1990

[54] 4-CYANO-4-(FLUOROPHENYL)-3-(SUBSTITUTED PHENYL) BUTYRIC ACIDS, ESTERS AND DERIVATIVES THEREOF, AND A METHOD OF SELECTIVELY CONTROLLING UNDESIRABLE VEGETATION IN RICE THEREWITH

[75] Inventors: Stephen S. Szucs, Trenton, N.J.; Laura S. Quakenbush, Yardley, Pa.; Pierre A. Marc, Willingboro, N.J.

[73] Assignee: American Cyanamid Company, Stamford, Conn.

[21] Appl. No.: 104,901

[22] Filed: Oct. 9, 1987

Related U.S. Application Data

[63] Continuation-in-part of Ser. No. 928,077, Nov. 6, 1986, abandoned.

[51] Int. Cl.[4] ............... A01N 43/08; A01N 37/34; C07D 307/46; C07C 121/66
[52] U.S. Cl. ............................... 71/105; 71/88; 558/404; 558/406
[58] Field of Search ............... 71/105, 88; 558/404, 558/406

[56] References Cited

U.S. PATENT DOCUMENTS

| | | | |
|---|---|---|---|
| 4,224,052 | 9/1980 | Szucs | 71/105 |
| 4,313,754 | 2/1982 | Szucs | 71/94 |
| 4,383,848 | 5/1983 | Szucs | 71/ |

OTHER PUBLICATIONS

Al-Arab, et al.; J. Chem. Eng. Data (1986), 31, pp. 261–262.

*Primary Examiner*—Joseph Paul Brust
*Attorney, Agent, or Firm*—Alice C. Brennan

[57] ABSTRACT

The invention relates to selective herbicidal 4-cyano-4-(fluorophenyl)-3-(substituted-phenyl)butyric acids, esters and derivatives thereof, and a method of selectively controlling undesirable vegetation in rice therewith.

38 Claims, No Drawings

4-CYANO-4-(FLUOROPHENYL)-3-(SUBSTITUTED PHENYL) BUTYRIC ACIDS, ESTERS AND DERIVATIVES THEREOF, AND A METHOD OF SELECTIVELY CONTROLLING UNDESIRABLE VEGETATION IN RICE THEREWITH

This application is a continuation-in-part of application, Ser. No. 06/928,077, filed November 6, 1986, now abandoned.

BACKGROUND OF THE INVENTION

Polysubstituted butyric acids, esters and derivatives of the general formula

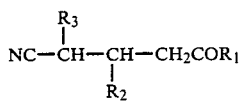

are described in U.S. Pat. Nos. 4,224,052; 4,313,754 and 4,383,848.

The threo isomers of these compounds are disclosed as being non-selective vegetation control agents while the erythro/threo isomer mixtures are disclosed as post-emergence herbicides having selectivity in certain crops such as corn, barley and wheat and as preemergence herbicides having selectivity in crops such as corn, cotton, soybeans, wheat and barley.

A method for the preparation of substituted-diaryl-cyanobutyrates by the condensation of ethyl cinnamates with benzyl cyanides has recently been reported by M. M. Al-Arab and A. M. Issa in *J. Chem. Eng. Data* 31, pp. 261–262 (1986).

While the references disclose post-emergence herbicidal activity in general for some of the compounds, they do not indicate that any would be useful selective herbicides for use in controlling undesirable vegetation in transplanted rice. Further, they do not indicate that in order to obtain selectivity for use in transplanted rice only certain specific substitution patterns for $R_2$ and $R_3$ in the general formula are effective.

It is an object of this invention to provide compounds which contain the specific substituents in both $R_2$ and $R_3$ which are required to obtain selectivity in rice. It is another object of this invention to provide a method for controlling undesirable vegetation selectively in the presence of rice utilizing these compounds.

SUMMARY OF THE INVENTION

The invention relates to selective herbicidal 4-cyano-4-(fluorophenyl)-3-(substituted-phenyl)butyric acids, esters and derivatives of formula I below

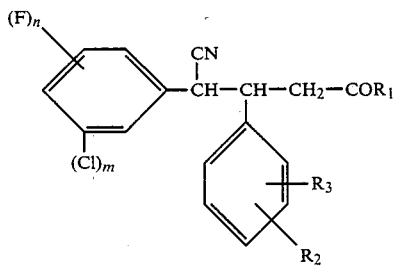

wherein $R_1$ is OH, $OR_4$ or OM; $R_2$ and $R_3$ are each hydrogen, fluorine, chlorine, bromine, iodine, $NO_2$, CN, $C_1$–$C_4$ alkyl, $C_1$–$C_4$ alkoxy, $OCHF_2$, $OCF_2CF_2H$, $OCF_3$, $CF_3$, $S(O)_XCH_3$ or $S(O)_XCF_2R_7$, wherein X is 0, 1 or 2 and $R_7$ is H, F, CHFCl, $CF_2H$ or $CF_3$; provided that $R_2$ and $R_3$ are not both hydrogen; n is an integer of one to five; m is zero or one; $R_4$ is alkyl $C_1$–$C_8$, monohaloalkyl $C_1$–$C_4$, hydroxyalkynyl $C_4$–$C_6$, monohaloalkynyl $C_4$–$C_6$, monohaloalkenyl $C_3$–$C_4$, furfuryl, benzyl or $C_1$–$C_4$ alkoxyethyl; M is an alkali metal, ammonium, $C_1$–$C_8$ mono or dialkylammonium or hydroxyethylammonium; and the stereoisomers thereof.

It has been found that the 4-cyano-3,4-diphenylbutyric acids, esters and derivatives thereof described above are effective herbicidal agents which may be used safely on rice. This result is surprising in light of the light level of herbicidal activity and lack of selectivity on rice of many of the compounds described in U.S. Pat. Nos. 4,224,052; 4,313,754 and 4,383,848.

DESCRIPTION OF THE PREFERRED EMBODIMENTS

The discovery that the selectivity in rice is obtained by substitution in both the phenyl ring at the C-4 position and the phenyl ring at the C-3 position of the butyric acid chain, and further that at least one fluorine must be present in the C-4 phenyl ring in the formula I cyanobutyric acid compounds of the present invention is unexpected. A preferred group of compounds are those of formula I wherein n is an integer of one or two; $R_2$ and $R_3$ are each hydrogen, bromine, chlorine, fluorine or methoxy provided that $R_2$ and $R_3$ are not both hydrogen.

Additionally, it has been found that methyl 3-(m-chlorophenyl)-4-cyano-4-(p-fluorophenyl)butyrate and other esters of this acid are unique in that they provide selective preemergence control of weeds in wheat and barley as well as selective weed control in rice.

Moreover, the compounds of formula I, besides controlling undesirable plant species selectively in the presence of rice, are found to modify or regulate the growth of desirable plant species. Such plant species include graminaceous species such as turf grasses and cereals as well as woody species such as fruit trees. The inhibition of vegetative plant growth in grasses is significant economically in areas requiring turf grass management by reducing the frequency of mowing and lowering the attendant overall maintenance costs. The reduction in the height of cereals is also important since a reduction in stem length can reduce or prevent lodging to facilitate harvesting and allow a greater realization of yield. Furthermore branching in woody species can be induced by breaking the apical dominance to promote the development of side shoots which, together with a reduction in height, is a very desirable feature in the cultivation of fruit trees and ornamentals. The use of the compounds of this invention in regulating the growth of plants is described in the co-pending application for U.S. patent application Ser. No. 928,076, filed 11/6/86, now abandoned.

The compounds of the invention may conveniently be applied as a solid or granular herbicidal compositions, comprising a herbicidally effective amount of a formula I polysubstituted butyric acid, ester or derivative, hereinabove defined, in admixture with an inert solid, water insoluble, diluent such as finely divided silica, kaolin, attapulgite, bentonite, montmorillonite, pumice, talc, fullers earth, diatomaceous earth, and the like. They may be applied as post transplant preemergence treatments, i.e., applied to the soil or to the floodwater after the rice has been transplanted, but prior to or shortly after the emergence of weeds; or as pre-plant incorporated treatments.

Certain of the formula I compounds may be applied by foliar application after the weeds have emerged, i.e., postemergence treatment, making them suitable for weed control in direct-seeded rice in addition to transplanted rice.

In practice, the erythro-threo stereoisometric mixtures are generally applied to the foliage and stems of undesirable plants or to soil or paddy floodwater containing seeds, seedlings or other propagating organs thereof, at a rate of application between about 0.032 and 11.2 kg per hectare of active ingredient.

The polysubstituted butyric acids, esters and derivatives of formula I, may be prepared as granular formulations containing, generally about 1% to 15% by weight of toxicant. The above compounds may also be formulated as wettable powders, emulsifiable concentrates, or flowable (thixotrophic) concentrates which are usually dispersed in water or other inexpensive liquid diluent for application as a liquid spray. Salts of the formula I compound which are water soluble may also be applied as aqueous solutions.

Wettable powder compositions can be prepared by grinding together about 15% to 80% by weight of a solid formula I compound, about 2% to 15% by weight of a surfactant such as sodium N-methyl-N-oleoyl taurate, alkyl phenoxy polyoxyethylene ethanol or sodium alkyl naphthalene sulfonate, and 18% to 65% by weight of a finely divided carrier such as kaolin attapulgite, diatomaceous earth, or the like.

A typical formulation prepared in accordance with the above description can be defined as follows:

66% by weight of formula I toxicant; 10% by weight of sodium salt of sulfated nonylphenoxypoly(ethyleneoxy)ethanol, and 24% by weight of precipitated silica.

Advantageously, flowable (thixotropic) concentrates can be prepared by grinding together 40% to 60% by weight of a solid formula I toxicant, 1% to 4% by weight of the sodium salt of condensed naphthalene sulfonic acids, 2% to 3% by weight of a gelling clay, 2% by weight of propylene glycol and from 54% to 32% by weight of water.

A typical granular formulation can be prepared by dissolving or dispersing the active compound in a solvent and applying the toxicant to a sorptive or nonsorptive carrier such as attapulgite, corn cob grits, limestone, silica, montmorillonite, bentonite or the like.

A typical emulsifiable concentrate can be prepared by admixing 13% by weight of the formula I compound with 6% by weight of a nonionic surfactant, such as a polyoxyethylene sorbitol ester, with 81% by weight of isophorone or 37% by weight of isophorone and 44% by weight of an aromatic petroleum distillate (bp 304°–330° F.) Sp.G. 15/56° C.=0.853–0.875.

The invention is further illustrated by the following non-limiting examples.

EXAMPLE 1

Preparation of erythro- and threo- methyl 4-cyano-3-(p-fluorophenyl)-4-(m-fluorophenyl)butyrate

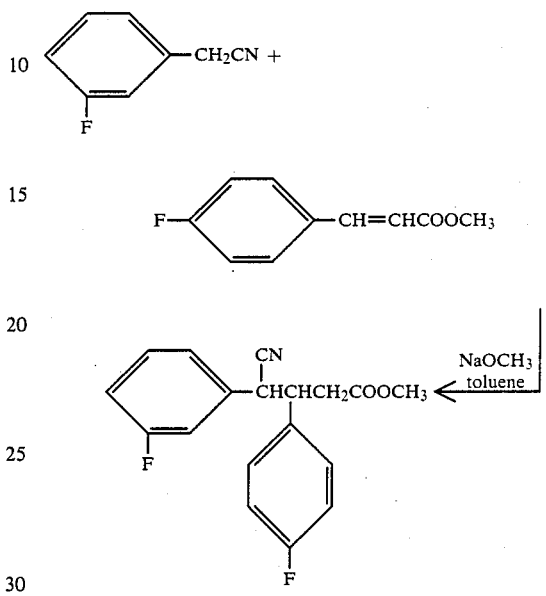

Sodium methoxide (3.0 g, 0.056 mol) is added in one portion to a stirred solution of m-fluorophenylacetonitrile (78.0 g, 0.577 mol) and methyl p-fluorocinnamate (100.0 g, 0.555 mol) in 700 mL of azeotropically dried toluene cooled in an ice bath under a nitrogen atmosphere. The reaction mixture is warmed to room temperature (18° C. to 24° C.) and stirred for five days. The mixture is concentrated under vacuum to yield a brown syrup which is partitioned between diethyl ether and water. The orange ether layer is washed three times with water, once with 1% aqueous hydrochloric acid, again with water and finally with a saturated aqueous sodium chloride solution. After stirring with magnesium sulfate, the filtrate is concentrated on a rotary evaporator using a water aspirator, followed by a vacuum pump at 0.5 mm Hg for eight hours. The title product is obtained in 95% yield (166.7 g) as a pinkish-orange semi-solid identified as an isomeric mixture of esters based on the proton and carbon magnetic resonance, infrared and chemical ionization mass spectra. The ratio of erythro/threo isomers is 62/38, respectively, based on the integrated areas of the CHCN doublets centered at δ4.38 (J=6 Hz) and 4.11 (J=7 Hz) ppm, respectively, in the proton nmr spectrum (CDCl$_3$). Thin layer chromatography on Merck Silica Gel 60 F-254 plates (CH$_2$Cl$_2$) shows two major spots which are not completely resolved. Gas-liquid chromatography (10% SP 2100 programmed at 125°/five minutes to 250°/30 minutes at a rate of 10°/minute) indicates a 93 relative area percent purity for the isomeric esters.

The corresponding ethyl ester is prepared by using ethyl p-fluorocinnamate and sodium ethoxide instead of methyl p-fluorocinnamate and sodium methoxide.

EXAMPLE 2

Preparation of erythro- and threo-4-cyano-3-(p-fluorophenyl)-4-(m-fluorophenyl)-butyric acid

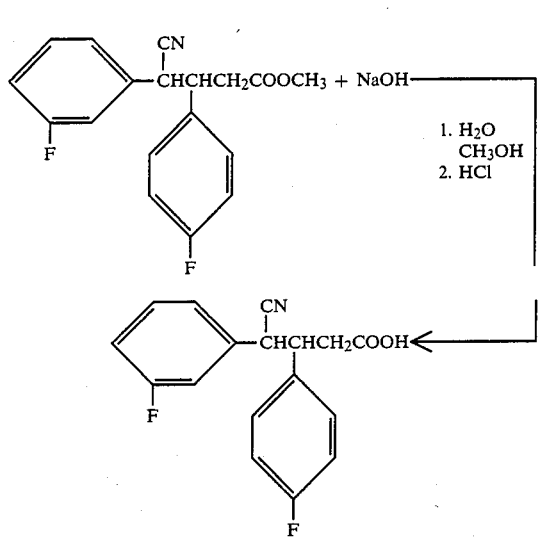

A solution of sodium hydroxide (18.3 g of 98.6% assay, 0.451 mol) in 230 mL of water is added dropwise over a one-hour period to a stirred solution of the ester (135.5 g of crude, 0.430 mol uncorrected) at room temperature. The resulting reddish-brown solution is heated at 50°–55° C. for two hours and thirty minutes and is stirred at room temperature overnight. After concentrating the mixture, the foamy brown syrup is partitioned between diethyl ether and water. The aqueous layer is extracted with five portions of ether and stirred under vacuum to remove residual ether to yield 736 mL of reddish amber aqueous solution. This solution is divided to prepare both the acid and the sodium salt. A volume of 579 mL (0.331 mol after correcting for 2.72 g of a red liquid, largely unreacted benzyl cyanide (nmr) isolatd from the ether extracts) of the aqueous solution is diluted with water to 750 mL and acidified by the dropwise addition of 10% HCl over a six-hour period. After stirring the resulting suspension at room temperature overnight, the white solids are collected, washed with water and dried in a vacuum oven at 45° to 50° C. to yield the title product, 97.2 g (97.4%) as a white powder having a melting point 110° (sinter), 128°–177° C. The product is identified by its chemical ionization mass spectrum, infrared spectrum and proton and carbon nmr spectrum. The ratio of isomers is determined to be erythro/threo=59/41 from the proton nmr spectrum. Thin layer chromatography ($CH_2Cl_2$) shows one major spot streaking from the baseline with only trace amounts of components having higher $R_f$ values.

EXAMPLE 3

Preparation of erythro- and threo- sodium 4-cyano-3-(p-fluorophenyl)-4-(m-fluorophenyl)butyrate

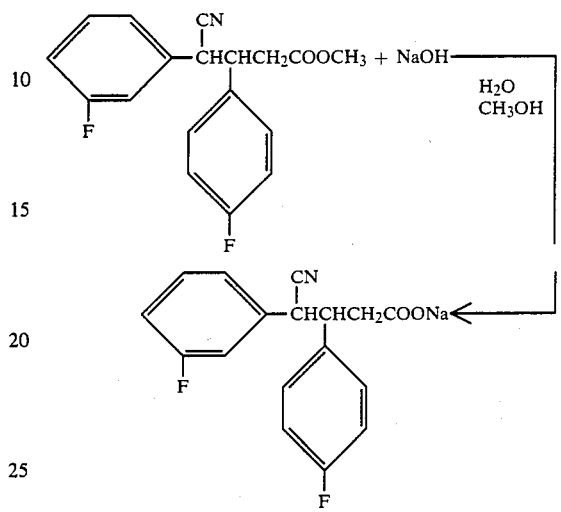

A portion of the aqueous solution of the hydrolyzed ester (157 mL, 0.090 mol) prepared in Example 2 is concentrated on a rotary evaporator. The resulting foamy viscous amber syrup is placed under a vacuum at <1 mm Hg for one day at a temperature of 50° to 55°. The glass which formed is pulverized with a mortar and pestle to yield 29.6 g light tan solids. Continued evacuation under the same conditions for an additional day with the sample on the rotary evaporator gives 28.8 g (99%) of the sodium salt with mp 138° C. (yellowing), 218° C. (sinter), 230°–235° C. The isomer ratio is found by proton nmr to be erythro/threo=57/43.

EXAMPLE 4

Separation of erythro- and threo-4-cyano-3-(p-fluorophenyl)-4-(m-fluorophenyl)-butyric acid

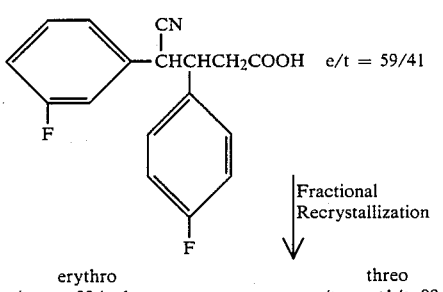

A suspension of an isomeric mixture of 4-cyano-3-(p-fluorophenyl)-4-(m-fluorophenyl)butyric acids (70.0 g, 0.232 mol, erythro/threo=59/41) in 1.4 l $CCl_4$ is heated at reflux for 30 minutes. The suspension is filtered to yield after drying 38.2 g of white solids and a pale yellow filtrate.

The white solids are recrystallized from 600 mL $CH_2Cl_2$ to yield 23.7 g (57.4% recovery of the amount of the erythro isomer present in the starting material) of fine white needles having mp 186° (sinter), 190.5–191.5° C. of the less-soluble, higher-melting erythro isomer by the proton and carbon magnetic resonance spectra, mass spectrum, and infrared spectrum.

The ratio of isomers, based on the CH methine doublets of the erythro isomer at δ4.70 (J=8 Hz) and the threo isomer at δ4.65 (J=8 Hz), respectively, in the proton nmr spectrum (DMSO-$d_6$), was erythro/threo=>99/<1.

The pale yellow filtrate from the original suspension is cooled to room temperature for one day to yield, after collecting, washing and drying, 18.2 g of white solids having an isomer ratio of erythro/threo=8/92 by proton nmr. A suspension of the solid is prepared in 200 mL $CCl_4$ which is heated at reflux for one hour, filtered, cooled to room temperature, and left standing for one day to give 17.2 g of a heterogeneous mixture of dull white granular crystals and brighter white needles. Physical separation gives 4.5 g of granular crystals which are recrystallized from 50 mL $CCl_4$ to yield 4.2 g (15% recovery of the amount of the threo isomer present in the starting material) of a mixture of crystals and needles. The sample is homogenized and identified as the more-soluble, lower-melting threo isomer by the proton and carbon resonance spectra, mass spectrum, infrared spectrum and mp 110.5° (sinter), 115°–121° C. The isomer ratio is determined to be erythro/threo=<1/>99 based on the proton nmr spectrum as previously described.

EXAMPLE 5

Preparation of threo- Methyl 4-cyano-3-(p-fluorophenyl)-4-(m-fluorophenyl)butyrate

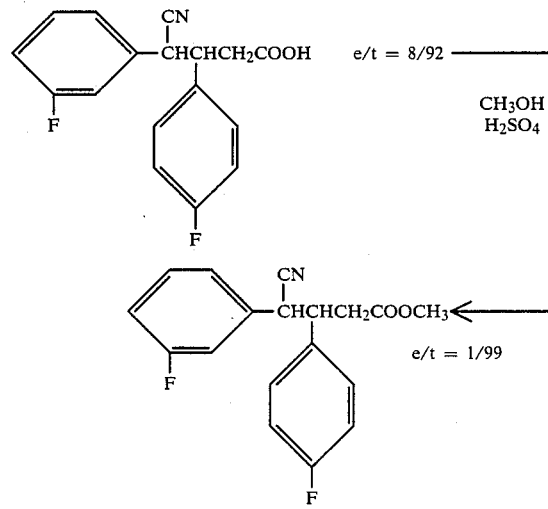

A suspension of an isomeric mixture of 4-cyano-3-(p-fluorophenyl)-4-(m-fluorophenyl)butyric acids (1.8 g, 5.9 mmol, erythro/threo=8/92) in 20 mL absolute MeOH containing 0.2 g concentrated $H_2SO_4$ is heated at reflux for 22 hours. After the reaction mixture is concentrated on a rotary evaporator, the resulting syrup is partitioned between methylene chloride and water. The methylene chloride layer is separated and washed three times with water, dried ($MgSO_4$), and concentrated to give 1.90 g of amber syrup. Flash chromatography on a column of silica gel using hexanes/$CH_2Cl_2$ (1/1) gives 0.90 g (48%) of a water-white syrup, identified as the title compound by the proton and carbon resonance spectrum, mass spectrum and infrared spectrum. The isomer ratio is determined to be erythro/threo=1/99 based on the proton nmr spectrum ($CDCl_3$) as previously described. (Other esters were similarly prepared using the appropriate alcohol).

EXAMPLE 6 to 66

Preparation of 4-cyano-4-(fluorophenyl)-3-(substituted-phenyl)butyric acids, esters and salts Utilizing the procedures of Examples one to five above and substituting the appropriately substituted fluorophenylacetonitrile for m-fluorophenylacetonitrile and alkyl-substituted cinnamate for methyl p-fluorocinnamate yields the 4-cyano-4-(fluorophenyl)-3-(substituted-phenyl)butyric acids, esters and salts listed in Tables I–III below.

TABLE I

4-Cyano-3-substituted phenyl-4-fluorophenylbutyric Acids

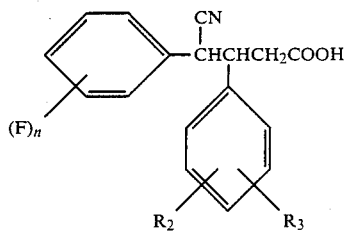

| Example | $R_2$ | $R_3$ | $(F)_n$ | Relative %* erythro | Relative %* threo | melting point (°C.) |
|---|---|---|---|---|---|---|
| 6 | m-Cl | H | m-F | 53 | 47 | 65 (sweating) 97–139 |
| 7 | p-F | H | p-F | 57 | 43 | 63 (sweating) 95–140 |
| 8 | m-Cl | H | p-F | 55 | 45 | 55 (sinter) 62–132 |
| 9 | m-F | H | p-F | 62 | 38 | 125 (sinter) 135–153 |
| 10 | m-Br | H | m-F | 60 | 40 | 63–70 |
| 11 | m-Br | H | p-F | 62 | 38 | 61–69 |
| 12 | m-F | H | m-F | 56 | 44 | 109–122 |
| 13 | o-F | H | m-F | 54 | 46 | 132–136 |
| 14 | 3,4-diF | | m-F | 57 | 43 | glass |
| 15 | m-Cl | H | 3,4-diF | 59 | 41 | 53–61 |
| 16 | 3,5-diCl | | p-F | 52 | 48 | 129–143 |
| 17 | m-$CF_3$ | H | p-F | 52 | 48 | 106–111 |
| 18 | m-$CF_3$ | H | m-F | 63 | 37 | 85–91 |
| 19 | p-Cl | H | m-F | 59 | 41 | 130–145 |
| 20 | 3,5-diCl | | m-F | 57 | 43 | 96 (sinter) 138–170 |
| 21 | 3-Cl—4-F | | m-F | 56 | 44 | orange semi-solid |
| 22 | 2,4-diF | | m-F | 55 | 45 | 119–131 |

*NMR(DMSO-$d_6$) δ C-4 CH doublet

TABLE II

Esters of 4-Cyano-3-substituted phenyl-4-fluorophenylbutyric Acids

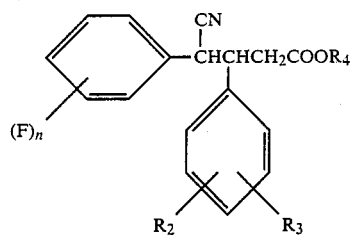

| Example | $R_2$ | $R_3$ | $(F)_n$ | $R_4$ | Relative %* erythro | threo | melting point (°C.) |
|---|---|---|---|---|---|---|---|
| 23 | p-Cl | H | p-F | $C_2H_5$ | 57 | 43 | viscous amber syrup |
| 24 | m-Cl | H | p-F | $C_2H_5$ | 27 | 73 | viscous amber syrup |
| 25 | p-F | H | m-F | $C_2H_5$ | 58 | 42 | viscous orange syrup |
| 26 | m-Cl | H | m-F | $C_2H_5$ | 57 | 43 | viscous orange syrup |
| 27 | p-F | H | p-F | $C_2H_5$ | 59 | 41 | brownish-yellow viscous syrup |
| 28 | m-Cl | H | p-F | $CH_3$ | 57 | 43 | viscous amber syrup |
| 29 | m-Cl | H | m-F | $CH_3$ | 60 | 40 | amber syrup |
| 30 | m-F | H | p-F | $CH_3$ | 57 | 43 | amber semi-solid |
| 31 | m-Br | H | m-F | $CH_3$ | 56 | 44 | yellow syrup |
| 32 | m-Br | H | p-F | $CH_3$ | 57 | 43 | yellow syrup |
| 33 | m-F | H | m-F | $CH_3$ | 57 | 43 | oily pale yellow solid |
| 34 | o-F | H | m-F | $CH_3$ | 53 | 47 | oily yellow solid |
| 35 | p-F | H | m-F | $CH_3$ | >99 | <1 | 107–108 |
| 36 | 3,4-diF |   | m-F | $C_2H_5$ | 61 | 39 | amber syrup |
| 37 | m-Cl | H | 3,4-diF | $CH_3$ | 56 | 44 | amber syrup |
| 38 | 3,5-diCl |   | p-F | $CH_3$ | 55 | 45 | colorless oil |
| 39 | m-$CF_3$ | H | p-F | $CH_3$ | 61 | 39 | yellow glassy solid |
| 40 | m-$CF_3$ | H | m-F | $CH_3$ | 65 | 35 | yellow glassy solid |
| 41 | p-Cl | H | m-F | $CH_3$ | 57 | 43 | 94–108 |
| 42 | m-Cl | H | p-F | i-Pr | 60 | 40 | yellow glassy solid |
| 43 | m-Cl | H | p-F | $C_2H_5$ | 57 | 43 | yellow glass |
| 44 | 3,4-diF |   | 3,4-diF | $CH_3$ | 60 | 40 | orange-yellow syrup |
| 45 | p-Cl | H | 3,4-diF | $CH_3$ | 58 | 42 | orange-yellow syrup |
| 46 | m-F | H | 3,4-diF | $CH_3$ | 53 | 47 | orange semi-solid |
| 47 | m-$OCHF_2$ | H | m-F | $CH_3$ | 59 | 41 | yellow oil |
| 48 | 3-Cl | 4-F | m-F | $CH_3$ | 57 | 43 | yellow oil |
| 49 | m-Cl | H | p-F | $CH_3$ | 99 | 1 | 99–101 |
| 50 | m-Cl | H | p-F | $CH_3$ | 1 | 99 | light yellow oil |
| 51 | 2,4-diF |   | m-F | $CH_3$ | 55 | 45 | 119–113 |
| 52 | m-Cl | H | p-F | $OCH_2CH_2OBu$ | 48 | 52 | yellow oil |

*NMR($CDCl_3$) δ C-4 CH doublet

TABLE III

Sodium Salts of 4-cyano-3-substituted phenyl-4-fluorophenylbutyric Acids

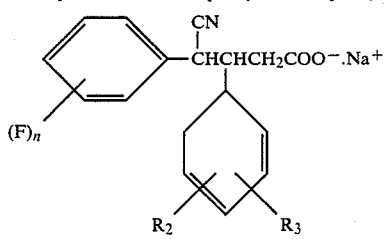

| Example | $R_2$ | $R_3$ | $(F)_n$ | Relative %* erythro | threo | melting point (°C.) |
|---|---|---|---|---|---|---|
| 53 | m-Cl | H | m-F | 58 | 42 | 192 (sinter) 242–255 (bubbling) |
| 54 | p-F | H | p-F | — | — | 117–143 (bubbling) |
| 55 | m-Cl | H | p-F | 61 | 39 | 154 (sinter) 270–276 (bubbling) |
| 56 | m-F | H | p-F | ~58 | ~42 | 230–235 |
| 57 | m-Br | H | m-F | 57 | 43 | >260 |
| 58 | m-Br | H | p-F | 54 | 46 | >260 |
| 59 | m-F | H | m-F | 55 | 45 | 233–236 |
| 60 | o-F | H | m-F | 55 | 45 | >240 |
| 61 | m-Cl | H | 3,4-diF | 54 | 46 | >260 |
| 62 | 3,5-diCl |   | p-F | 54 | 46 | >260 |
| 63 | m-$CF_3$ | H | p-F | 56 | 44 | white tacky solid |
| 64 | m-$CF_3$ | H | m-F | 61 | 39 | >215 |

TABLE III-continued
Sodium Salts of 4-cyano-3-substituted phenyl-4-fluorophenylbutyric Acids

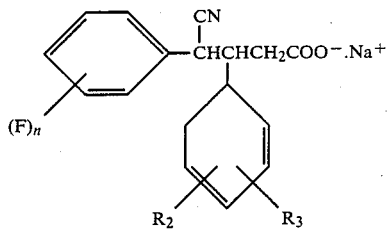

| Example | R₂ | R₃ | (F)ₙ | Relative %* erythro | threo | melting point (°C.) |
|---|---|---|---|---|---|---|
| 65 | p-Cl | H | m-F | 57 | 43 | orange tacky solid |
| 66 | p-Cl | H | 3,5-diCl | 69 | 31 | >245 |

*NMR(D₂O) δ C-4 CH doublet or δ from proton-decoupled C-13 spectra

EXAMPLE 67

Preparation of the diisopropylamine salt of erythro- and threo-4-cyano-3-(p-fluorophenyl)-4-(m-fluorophenyl)-butyric acid

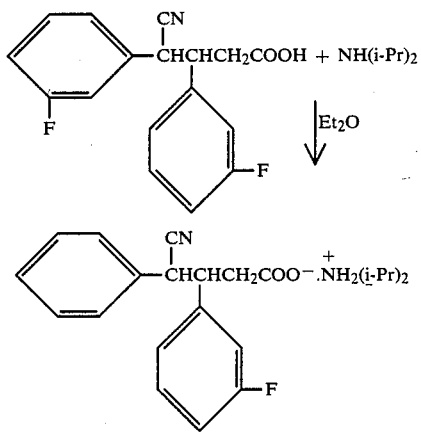

Diisopropylamine (0.26 g, 2.6 mmol) is added dropwise with stirring to a solution of erythro- and threo-4-cyano-3-(p-fluorophenyl)-4-(m-fluorophenyl)butyric acid (0.77 g, 2.6 mmol) in 5 mL anhydrous ether. The solution is stirred overnight under a nitrogen atmosphere. The resulting milky suspension is concentrated to a white solid and dried under vacuum at 50° to give 1.00 g (96%) of the title salt which had a melting point of 138°-143° C. The proton nmr spectrum indicated a ratio of erythro/threo=54/46.

EXAMPLE 68

Preemergence herbicidal activity

The preemergence herbicidal activity of the compounds of the present invention is exemplified by the following tests in which the seeds or propagating organs of a variety of monocotyledonous and dicotyledonous plants, including important weeds in transplanted rice culture, are planted in separate cups and covered with approximately 2.5 cm of soil. After planting, the cups are sprayed with the selected aqueous acetone solution containing test compound in sufficient quantity to provide the equivalent of about 0.063 kg to 2 kg per hectare of test compound per cup. The treated cups are then placed on greenhouse benches, watered and cared for in accordance with conventional greenhouse procedures. Three to five weeks after treatment, the tests are terminated and each cup is examined and rated according to the rating system provided below. The data obtained are reported in Table IV below.

| Rating System | | |
|---|---|---|
| Rating | Meaning | % Control (compared to check) |
| 0 | No effect | 0 |
| 1 | Trace effect | 1-5 |
| 2 | Slight effect | 6-15 |
| 3 | Moderate effect | 16-29 |
| 4 | Injury | 30-44 |
| 5 | Definite injury | 45-64 |
| 6 | Herbicidal effect | 65-79 |
| 7 | Good herbicidal effect | 80-90 |
| 8 | Approaching complete kill | 91-99 |
| 9 | Complete kill | 100 |

*Based on visual determination of stand, size, vigor, chlorosis, growth malformation and over-all plant appearance.

| Plant abbreviations, common name and scientific name | | |
|---|---|---|
| BA | barnyardgrass | (Echinochloa crus-galli (L.) Beauv.) |
| BG | blackgrass | (Alopecurus myosuroides Huds.) |
| CH | cheat | (Bromus secalinus L.) |
| FO | green foxtail | (Setaria viridis (L.) Beauv.) |
| PN | purple nutsedge | (Cyperus rotundus L.) |
| WO | wild oats | (Avena fatua L.) |
| ST | sprangletop | (Leptochloa filiformis (Lam.) Beauv.) |
| MA | matricaria | (Matricaria spp) |
| WM | wild mustard | (Sinapis arvensis L.) |
| SE | sesbania | (Sesbania exaltata (Raf.) Rydb. ex A. W. Hill) |
| VL | velvetleaf | (Abutilon theophrasti (Medik.) |
| BR | bulrush | (Scirpus spp) |

TABLE IV

PRE-EMERGENCE TESTS - RATES IN KG/HA

| Compound of EXAMPLE | Rate | BA | BG | CH | FO | PN | WO | ST | MA | WM | SE | VL | BR |
|---|---|---|---|---|---|---|---|---|---|---|---|---|---|
| 1 | 1.000 | 7.5 | 9.0 | — | 9.0 | 8.5 | 8.0 | 7.0 | 5.0 | 8.0 | — | 5.0 | 6.0 |
|   | .500 | 7.5 | 8.0 | — | 7.0 | 8.0 | 6.0 | 4.0 | 0.0 | 8.0 | — | 0.0 | 3.5 |
|   | .250 | 5.5 | 8.0 | — | 6.0 | 4.5 | 5.0 | 4.0 | 0.0 | 6.0 | — | 0.0 | 1.0 |
|   | .125 | 3.0 | 0.0 | — | 5.0 | 2.0 | 3.0 | 2.0 | 0.0 | 6.0 | — | 0.0 | 1.0 |
| 2 | 1.000 | 6.3 | — | — | — | 8.1 | — | 8.6 | — | — | 5.2 | — | 6.4 |
|   | .500 | 5.6 | — | — | — | 9.0 | — | 6.3 | — | — | 2.2 | — | 4.7 |
|   | .250 | 3.3 | — | — | — | 7.5 | — | 3.9 | — | — | 0.6 | — | 2.9 |
|   | .125 | 1.4 | — | — | — | 3.1 | — | 2.0 | — | — | 0.0 | — | 1.0 |
| 3 | 1.000 | 4.5 | — | — | — | 9.0 | — | 7.5 | — | — | — | — | 7.5 |
|   | .500 | 3.0 | — | — | — | 6.0 | — | 3.0 | — | — | — | — | 3.0 |
|   | .250 | 1.0 | — | — | — | 3.5 | — | 1.0 | — | — | — | — | 1.0 |
|   | .125 | 0.5 | — | — | — | 1.0 | — | 0.0 | — | — | — | — | 0.0 |
| 4-erythro | 1.000 | 0.0 | — | — | — | 4.0 | — | 0.0 | — | — | 0.0 | — | 0.0 |
|   | .500 | 0.0 | — | — | — | 4.0 | — | 0.0 | — | — | 0.0 | — | 0.0 |
|   | .250 | 0.0 | — | — | — | 0.0 | — | 0.0 | — | — | 0.0 | — | 0.0 |
|   | .125 | 0.0 | — | — | — | 0.0 | — | 0.0 | — | — | 0.0 | — | 0.0 |
| 5 | 1.000 | 9.0 | — | — | — | 9.0 | — | 9.0 | — | — | 8.0 | — | 7.0 |
|   | .500 | 9.0 | — | — | — | 9.0 | — | 9.0 | — | — | 7.0 | — | 7.0 |
|   | .250 | 9.0 | — | — | — | 8.0 | — | 9.0 | — | — | 5.0 | — | 6.0 |
|   | .125 | 9.0 | — | — | — | 6.0 | — | 8.0 | — | — | 5.0 | — | 2.0 |
| 6 | 1.000 | 9.0 | — | — | — | 6.0 | — | 9.0 | — | — | — | — | 2.0 |
|   | .500 | 9.0 | — | — | — | 4.0 | — | 9.0 | — | — | — | — | 2.0 |
|   | .250 | 1.0 | — | — | — | — | — | 9.0 | — | — | — | — | 2.0 |
|   | .125 | 0.0 | — | — | — | 0.0 | — | 8.0 | — | — | — | — | 0.0 |
| 7 | 1.000 | 9.0 | — | — | — | 8.0 | — | 9.0 | — | — | — | — | 9.0 |
|   | .500 | 0.0 | — | — | — | — | — | 2.0 | — | — | — | — | 7.0 |
|   | .250 | 0.0 | — | — | — | 0.0 | — | 0.0 | — | — | — | — | 0.0 |
|   | .125 | 0.0 | — | — | — | 0.0 | — | 0.0 | — | — | — | — | 0.0 |
| 8 | 1.000 | 4.0 | 8.0 | 6.0 | 9.0 | 6.0 | 9.0 | 9.0 | 9.0 | 9.0 | — | — | 8.0 |
|   | .500 | 4.0 | 5.0 | 6.0 | 9.0 | — | 5.0 | 9.0 | 9.0 | 9.0 | — | — | 8.0 |
|   | .250 | — | 2.0 | 5.0 | 4.0 | 6.0 | 4.0 | — | 4.0 | 9.0 | — | — | 6.0 |
|   | .125 | 0.0 | 0.0 | 2.0 | 0.0 | 0.0 | 0.0 | 0.0 | 0.0 | 9.0 | — | — | 0.0 |
| 9 | 1.000 | 5.7 | 6.0 | 9.0 | 9.0 | 9.0 | 6.0 | 5.0 | 4.0 | 8.0 | 8.0 | — | 9.0 |
|   | .500 | 3.7 | 6.0 | 7.0 | 3.0 | 9.0 | 4.0 | 2.0 | 6.0 | 7.0 | 7.0 | — | 7.0 |
|   | .250 | 2.0 | 5.0 | 6.0 | 1.0 | 6.0 | 3.0 | 0.0 | 3.0 | 8.0 | 3.0 | — | 4.5 |
|   | .125 | 1.3 | 5.0 | 5.0 | 0.0 | 3.0 | 2.0 | 0.0 | 2.0 | 6.0 | 2.0 | — | 3.0 |
| 10 | 1.000 | 5.3 | 9.0 | 7.0 | 3.0 | 5.5 | 6.0 | 9.0 | 2.0 | 9.0 | 9.0 | — | 6.0 |
|   | .500 | 4.3 | 7.0 | — | 2.0 | 5.5 | 4.0 | 7.5 | 2.0 | 8.0 | 4.0 | — | 4.5 |
|   | .250 | 2.0 | 4.0 | 6.0 | 1.0 | 2.0 | 2.0 | 5.5 | 0.0 | 8.0 | 1.0 | — | 3.5 |
|   | .125 | 1.3 | 4.0 | 6.0 | 0.0 | 2.0 | 0.0 | 3.0 | 0.0 | 7.0 | 0.0 | — | 2.5 |
| 11 | 1.000 | 4.0 | 5.0 | 9.0 | 9.0 | 3.5 | 7.0 | 7.5 | 5.0 | 9.0 | 6.0 | — | 4.5 |
|   | .500 | 1.3 | 4.0 | 6.0 | 0.0 | 2.0 | 4.0 | 2.0 | 4.0 | 9.0 | 3.0 | — | 2.0 |
|   | .250 | 0.7 | 2.0 | 5.0 | 0.0 | 1.0 | 0.0 | 0.0 | 0.0 | 9.0 | 2.0 | — | 1.0 |
|   | .125 | 0.0 | — | 4.0 | 0.0 | 1.0 | 0.0 | 0.0 | 0.0 | 9.0 | 1.0 | — | 1.0 |
| 12 | 1.000 | 7.0 | 9.0 | 9.0 | 9.0 | 9.0 | 9.0 | 8.5 | 6.0 | 8.5 | 9.0 | — | 6.2 |
|   | .500 | 6.3 | 9.0 | 9.0 | 9.0 | 8.0 | 8.0 | 6.5 | 5.0 | 8.0 | 6.5 | — | 5.0 |
|   | .250 | 3.7 | 6.0 | 9.0 | 6.0 | 6.0 | 7.0 | 5.5 | 4.0 | 8.0 | 4.5 | — | 3.0 |
|   | .125 | 3.3 | 5.0 | 9.0 | — | 2.0 | 5.0 | 2.0 | 5.0 | 8.0 | 1.0 | — | 1.8 |
| 13 | 1.000 | 8.3 | 9.0 | 9.0 | 9.0 | 8.8 | 9.0 | 8.5 | 6.0 | 8.5 | 8.5 | 8.0 | 4.5 |
|   | .500 | 6.7 | 9.0 | 9.0 | 9.0 | 6.0 | 8.0 | 9.0 | 6.0 | 8.0 | 7.5 | — | 5.0 |
|   | .250 | 5.0 | 8.0 | 9.0 | 6.0 | 5.7 | 7.0 | 5.0 | 5.0 | 8.0 | 4.0 | — | 3.0 |
|   | .125 | 2.0 | 6.0 | 9.0 | 6.0 | 4.3 | 6.0 | 1.0 | 5.0 | 8.0 | 3.5 | — | 1.5 |
| 14 | 1.000 | 5.8 | 8.0 | 9.0 | 9.0 | 8.0 | 7.0 | 6.0 | 5.0 | 8.0 | 1.3 | — | 2.7 |
|   | .500 | 4.3 | 8.0 | 9.0 | 9.0 | 5.0 | 6.0 | 6.0 | 5.0 | 8.0 | 0.3 | — | 4.3 |
|   | .250 | 1.8 | 5.0 | 9.0 | 3.0 | 3.3 | 4.0 | 3.3 | 4.0 | 8.0 | 0.3 | — | 2.7 |
|   | .125 | 1.8 | 5.0 | 9.0 | 2.0 | 1.3 | 3.0 | 1.7 | 2.0 | 8.0 | 0.3 | — | 2.0 |
| 15 | 1.000 | 8.0 | 6.0 | 7.0 | 7.0 | 7.0 | 6.0 | 9.0 | 7.0 | 8.0 | 4.0 | — | 6.0 |
|   | .500 | 4.5 | 5.0 | 6.0 | 8.0 | 6.0 | 5.0 | 9.0 | 5.0 | 8.0 | 4.0 | — | 5.0 |
|   | .250 | 2.5 | 4.0 | 6.0 | 6.0 | 3.0 | 2.0 | 8.0 | 2.0 | 8.0 | 0.0 | — | 4.0 |
|   | .125 | 2.5 | 3.0 | 4.0 | 3.0 | 0.0 | 1.0 | 2.0 | 2.0 | 6.0 | 0.0 | — | 3.0 |
| 16 | 1.000 | 5.5 | 8.0 | 8.0 | 9.0 | 1.0 | 6.0 | 6.0 | 6.0 | 9.0 | 2.0 | — | 1.0 |
|   | .500 | 2.5 | 5.0 | 6.0 | 8.0 | 1.0 | 5.0 | 2.0 | 4.0 | 8.0 | 0.0 | — | 0.0 |
|   | .250 | 2.0 | 2.0 | 5.0 | 1.0 | 0.0 | 3.0 | 0.0 | 1.0 | 8.0 | 0.0 | — | 0.0 |
|   | .125 | 0.5 | 0.0 | 1.0 | 0.0 | 0.0 | 0.0 | 0.0 | 0.0 | 4.0 | 0.0 | — | 0.0 |
| 17 | 1.000 | 3.0 | 5.0 | 6.0 | 5.0 | 4.0 | 5.0 | 0.0 | 5.0 | 8.0 | 2.0 | — | 4.0 |
|   | .500 | 1.0 | 2.0 | 5.0 | 2.0 | 1.0 | 3.0 | 0.0 | 2.0 | 8.0 | 0.0 | — | 1.0 |
|   | .250 | 0.0 | 1.0 | 5.0 | 0.0 | 0.0 | 1.0 | 0.0 | 0.0 | 8.0 | 0.0 | — | 0.0 |
|   | .125 | 0.0 | 0.0 | 2.0 | 0.0 | 0.0 | 0.0 | 0.0 | 0.0 | 3.0 | 0.0 | — | 0.0 |
| 18 | 1.000 | 3.0 | 5.0 | 6.0 | 4.0 | 2.0 | 5.0 | 0.0 | 1.0 | 8.0 | 0.0 | — | 2.0 |
|   | .500 | 2.5 | 5.0 | — | 4.0 | 0.0 | 4.0 | 0.0 | 1.0 | 8.0 | 0.0 | — | 1.0 |
|   | .250 | 1.0 | 4.0 | 3.0 | 3.0 | 0.0 | 2.0 | 0.0 | 1.0 | 8.0 | 0.0 | — | 0.0 |
|   | .125 | 0.5 | 2.0 | 2.0 | 0.0 | 0.0 | 0.0 | 0.0 | 1.0 | 4.0 | 0.0 | — | 0.0 |
| 19 | 1.000 | 6.5 | 9.0 | 9.0 | 9.0 | 9.0 | 9.0 | 9.0 | 7.0 | 8.0 | 7.0 | — | 8.0 |
|   | .500 | 6.5 | 9.0 | 9.0 | 9.0 | 9.0 | 7.0 | 9.0 | 6.0 | 8.0 | — | — | 7.0 |
|   | .250 | 3.5 | 8.0 | 9.0 | 6.0 | 4.0 | 6.0 | 2.0 | 5.0 | 8.0 | 4.0 | — | 4.0 |
|   | .125 | 3.0 | 6.0 | 6.0 | 5.0 | 0.0 | 4.0 | 0.0 | 4.0 | 8.0 | 0.0 | — | 2.0 |
| 20 | 1.000 | 5.5 | 9.0 | 7.0 | 9.0 | 6.0 | 7.0 | 9.0 | 5.0 | 9.0 | 7.0 | — | 2.0 |
|   | .500 | 4.0 | 7.0 | 7.0 | 6.0 | 2.0 | 5.0 | 9.0 | 5.0 | 9.0 | 2.0 | — | 1.0 |
|   | .250 | 3.5 | 6.0 | 7.0 | 4.0 | 1.0 | 4.0 | 2.0 | 0.0 | 8.0 | 2.0 | — | 1.0 |

TABLE IV-continued

PRE-EMERGENCE TESTS - RATES IN KG/HA

| Compound of EXAMPLE | Rate | BA | BG | CH | FO | PN | WO | ST | MA | WM | SE | VL | BR |
|---|---|---|---|---|---|---|---|---|---|---|---|---|---|
| | .125 | 2.5 | 4.0 | 4.0 | 2.0 | 1.0 | 3.0 | 0.0 | 0.0 | 8.0 | 2.0 | — | 0.0 |
| | 1.000 | 3.0 | 9.0 | 9.0 | 9.0 | 0.0 | 6.0 | 0.0 | 4.0 | 9.0 | 0.0 | — | 0.0 |
| 21 | .500 | 1.5 | 8.0 | 9.0 | 0.0 | 0.0 | 6.0 | 0.0 | 0.0 | 6.0 | 0.0 | — | 0.0 |
| | .250 | 0.0 | 0.0 | 4.0 | 0.0 | 0.0 | 3.0 | 0.0 | 0.0 | 8.0 | 0.0 | — | 0.0 |
| | .125 | 0.0 | 0.0 | 0.0 | 0.0 | 0.0 | 0.0 | 0.0 | 0.0 | 3.0 | 0.0 | — | 0.0 |
| | 1.000 | 3.5 | 9.0 | 9.0 | 7.0 | 8.0 | 7.0 | 9.0 | 1.0 | 9.0 | 4.0 | — | 6.0 |
| 22 | .500 | 3.0 | 7.0 | 9.0 | 7.0 | 9.0 | 7.0 | 2.0 | 0.0 | 9.0 | 4.0 | — | 6.0 |
| | .250 | 2.0 | 7.0 | 6.0 | 5.0 | 4.0 | 5.0 | 0.0 | 0.0 | 8.0 | 0.0 | — | 0.0 |
| | .125 | 1.5 | 6.0 | 5.0 | 0.0 | 2.0 | 3.0 | 0.0 | 0.0 | 4.0 | 0.0 | — | 0.0 |
| | 1.000 | 6.5 | 9.0 | — | 9.0 | 6.3 | 9.0 | 9.0 | — | 9.0 | 0.0 | 3.0 | 3.0 |
| 23 | .500 | 5.5 | 9.0 | — | 9.0 | 2.7 | 8.0 | 8.5 | — | 9.0 | 0.0 | 3.0 | 1.0 |
| | .250 | 5.0 | 8.0 | — | 8.0 | 1.0 | 4.0 | 6.5 | — | 9.0 | 0.0 | 0.0 | 2.0 |
| | .125 | 3.0 | 6.0 | — | 8.0 | 0.0 | 1.0 | 0.0 | — | 8.0 | 0.0 | 0.0 | 0.0 |
| | 1.000 | 9.0 | — | — | 9.0 | 6.5 | 8.0 | 9.0 | — | 9.0 | — | 8.0 | 9.0 |
| 24 | .500 | 9.0 | — | — | 9.0 | 4.0 | 6.5 | 9.0 | — | 8.5 | — | 4.0 | 9.0 |
| | .250 | 9.0 | — | — | 9.0 | 2.5 | 3.0 | 9.0 | — | 3.0 | — | 0.0 | 9.0 |
| | .125 | 9.0 | — | — | 9.0 | 1.0 | 0.0 | 4.0 | — | 0.0 | — | 0.0 | 4.0 |
| | 1.000 | 9.0 | 8.0 | — | 9.0 | 8.8 | 8.5 | 9.0 | — | 9.0 | — | 7.0 | 8.7 |
| 25 | .500 | 8.0 | 7.0 | — | 8.5 | 7.5 | 7.5 | 9.0 | — | 9.0 | — | 5.0 | 6.0 |
| | .250 | 3.7 | 6.0 | — | 7.5 | 5.3 | 3.5 | 8.3 | — | 7.0 | — | 1.0 | 2.3 |
| | .125 | 0.7 | 0.0 | — | 2.0 | 1.5 | 0.5 | 4.0 | — | 5.0 | — | 0.0 | 0.7 |
| | 1.000 | 7.6 | — | — | 9.0 | 5.0 | 9.0 | 8.6 | — | 9.0 | 4.2 | 4.0 | 5.5 |
| 26 | .500 | 8.0 | — | — | 9.0 | 3.8 | 9.0 | 8.3 | — | 9.0 | — | 1.0 | 4.8 |
| | .250 | 4.0 | — | — | 9.0 | 2.0 | 7.0 | 7.3 | — | 8.0 | — | 0.0 | 2.0 |
| | .125 | 3.3 | — | — | 9.0 | 0.4 | 6.0 | 5.3 | — | 7.0 | — | 0.0 | 1.0 |
| | 1.000 | 5.0 | — | — | — | 9.0 | — | 9.0 | — | — | — | — | 9.0 |
| 27 | .500 | 0.0 | — | — | — | 2.0 | — | 2.0 | — | — | — | — | 3.0 |
| | .250 | 0.0 | — | — | — | 0.0 | — | 0.0 | — | — | — | — | 0.0 |
| | .125 | 0.0 | — | — | — | 0.0 | — | 0.0 | — | — | — | — | 0.0 |
| | 1.000 | 7.4 | 9.0 | 8.4 | 9.0 | 5.0 | 8.8 | 8.8 | 5.3 | 8.9 | 6.0 | 8.0 | 5.5 |
| 28 | .500 | 5.0 | 8.4 | 7.7 | 8.4 | 2.0 | 7.1 | 8.3 | 4.0 | 8.3 | 0.5 | 7.0 | 2.3 |
| | .250 | 2.4 | 4.7 | 5.1 | 7.4 | 1.0 | 2.1 | 6.3 | 0.4 | 7.6 | 0.0 | 4.0 | 1.8 |
| | .125 | 2.1 | 3.2 | 3.7 | 5.0 | 0.0 | 0.3 | 4.5 | 0.5 | 7.0 | 0.0 | — | 0.3 |
| | 1.000 | 8.3 | 9.0 | — | 9.0 | 4.5 | 8.0 | 7.0 | 6.0 | 9.0 | — | 6.0 | 2.5 |
| 29 | .500 | 6.5 | 9.0 | — | 9.0 | 4.5 | 8.0 | 8.0 | 0.0 | 8.0 | — | 4.0 | 0.0 |
| | .250 | 4.0 | 8.0 | — | 9.0 | 3.0 | 7.0 | 8.0 | 0.0 | 8.0 | — | 1.0 | 0.0 |
| | .125 | 2.0 | 0.0 | — | 7.0 | 1.0 | 6.0 | 4.0 | 0.0 | 8.0 | — | 0.0 | 0.0 |
| | 1.000 | 9.0 | 9.0 | 8.0 | 9.0 | 9.0 | 9.0 | 9.0 | 7.0 | 8.5 | 8.5 | 7.0 | 8.5 |
| 30 | .500 | 9.0 | 9.0 | 9.0 | 9.0 | 6.5 | 7.0 | 9.0 | 6.0 | 9.0 | 6.0 | — | 8.0 |
| | .250 | 5.3 | 7.0 | 6.0 | 9.0 | 6.5 | 4.0 | 8.5 | 6.0 | 8.0 | 3.0 | — | 6.5 |
| | .125 | 3.7 | 7.0 | 4.0 | 3.0 | 4.0 | 1.0 | 6.0 | 4.0 | 5.0 | 0.0 | — | 4.0 |
| | 1.000 | 7.7 | 9.0 | 6.0 | 9.0 | 3.0 | 9.0 | 9.0 | 2.0 | 9.0 | 7.4 | — | 3.0 |
| 31 | .500 | 7.0 | 7.0 | 6.0 | 9.0 | 3.0 | 9.0 | 9.0 | 0.0 | 9.0 | 3.0 | — | 1.5 |
| | .250 | 2.7 | 7.0 | 5.0 | 2.0 | 1.0 | 5.0 | 9.0 | 0.0 | 8.0 | 0.5 | — | 1.0 |
| | .125 | 2.0 | 6.0 | 5.0 | 8.0 | 1.0 | 3.0 | 7.0 | 0.0 | 7.0 | 0.0 | — | 0.0 |
| | 1.000 | 6.7 | 8.0 | 7.0 | 9.0 | 2.0 | 7.0 | 9.0 | 3.0 | 9.0 | 9.0 | — | 7.0 |
| 32 | .500 | 4.3 | 7.0 | 7.0 | 6.0 | 2.0 | 2.0 | 9.0 | 4.0 | 9.0 | 1.5 | — | 3.0 |
| | .250 | 2.7 | 4.0 | 4.0 | 5.0 | 1.5 | 0.0 | 8.0 | 2.0 | 9.0 | 0.5 | — | 0.0 |
| | .125 | 1.3 | 3.0 | 3.0 | 3.0 | 1.0 | 0.0 | 3.0 | 2.0 | 7.0 | 0.5 | — | 0.0 |
| | 1.000 | 9.0 | 9.0 | 9.0 | 9.0 | 8.4 | 9.0 | 9.0 | 6.0 | 8.7 | 7.6 | 6.0 | 8.9 |
| 33 | .500 | 9.0 | 9.0 | 9.0 | 9.0 | 8.4 | 9.0 | 9.0 | 6.0 | 8.3 | 6.3 | 6.0 | 7.1 |
| | .250 | 7.0 | 8.0 | 9.0 | 9.0 | 6.0 | 7.4 | 9.0 | 3.5 | 8.0 | 2.5 | — | 4.6 |
| | .125 | 6.8 | 9.0 | 9.0 | 7.5 | 3.4 | 6.0 | 8.0 | 2.5 | 7.5 | 0.3 | — | 2.9 |
| | 1.000 | 8.8 | 9.0 | 9.0 | 9.0 | 8.0 | 9.0 | 9.0 | 6.0 | 8.0 | 9.0 | 8.0 | 5.4 |
| 34 | .500 | 9.0 | 9.0 | 9.0 | 9.0 | 5.3 | 9.0 | 9.0 | 6.0 | 8.0 | 5.5 | — | 4.3 |
| | .250 | 7.7 | 8.0 | 9.0 | 9.0 | 3.7 | 7.0 | 9.0 | 4.0 | 7.0 | 4.5 | — | 3.0 |
| | .125 | 5.3 | 5.0 | 6.0 | 9.0 | 2.3 | 5.0 | 8.0 | 5.0 | 7.0 | 2.0 | — | 1.5 |
| | 1.000 | 0.0 | — | — | — | 0.0 | — | 0.0 | — | — | 0.0 | — | 0.0 |
| 35 | .500 | 0.0 | — | — | — | 0.0 | — | 0.0 | — | — | 0.0 | — | 0.0 |
| | .250 | 0.0 | — | — | — | 0.0 | — | 0.0 | — | — | 0.0 | — | 0.0 |
| | .125 | 0.0 | — | — | — | 0.0 | — | 0.0 | — | — | 0.0 | — | 0.0 |
| | 1.000 | 8.3 | 9.0 | 9.0 | 9.0 | 8.0 | 9.0 | 8.7 | 4.0 | 8.0 | 1.3 | — | 5.7 |
| 36 | .500 | 4.0 | 9.0 | 6.0 | 9.0 | 7.0 | 7.0 | 7.3 | 3.0 | 9.0 | 0.7 | — | 4.0 |
| | .250 | 2.5 | 6.0 | 7.0 | 6.0 | 4.0 | 4.0 | 3.3 | 2.0 | 8.0 | 0.7 | — | 1.3 |
| | .125 | 1.0 | 4.0 | 8.0 | 6.0 | 2.7 | 2.0 | 2.0 | 2.0 | 7.0 | 0.3 | — | 0.7 |
| | 1.000 | 9.0 | 9.0 | 8.5 | 9.0 | 6.0 | 9.0 | 9.0 | 8.0 | 9.0 | 6.0 | — | 8.0 |
| 37 | .500 | 9.0 | 9.0 | 8.5 | 9.0 | 3.7 | 8.0 | 9.0 | 7.0 | 9.0 | 2.0 | — | 7.0 |
| | .250 | 7.0 | 9.0 | 8.0 | 8.0 | 2.0 | 5.5 | 9.0 | 5.0 | 9.0 | 0.0 | — | 3.0 |
| | .125 | 6.5 | 9.0 | 2.5 | 7.0 | 0.7 | 3.0 | 9.0 | 5.0 | 8.0 | 0.0 | — | 1.0 |
| | 1.000 | 9.0 | 9.0 | 8.0 | 9.0 | 2.0 | 7.0 | 9.0 | 3.0 | 9.0 | 0.0 | — | 2.0 |
| 38 | .500 | 8.5 | 6.0 | 7.0 | 9.0 | 0.0 | 7.0 | 9.0 | 2.0 | 9.0 | 0.0 | — | 1.0 |
| | .250 | 4.0 | 5.0 | 3.0 | 6.0 | 0.0 | 1.0 | 9.0 | 0.0 | 7.0 | 0.0 | — | 0.0 |
| | .125 | 3.0 | 2.0 | 0.0 | 6.0 | 0.0 | 0.0 | 2.0 | 0.0 | 8.0 | 0.0 | — | 0.0 |
| | 1.000 | 2.0 | 9.0 | 6.0 | 9.0 | 1.0 | 8.0 | 0.0 | 1.0 | 9.0 | 0.0 | — | 2.0 |
| 39 | .500 | 1.5 | 6.0 | 6.0 | 9.0 | 0.0 | 6.0 | 0.0 | 1.0 | 9.0 | 0.0 | — | 0.0 |
| | .250 | 0.5 | 6.0 | 5.0 | 9.0 | 0.0 | 3.0 | 0.0 | 1.0 | 9.0 | 0.0 | — | 0.0 |
| | .125 | 0.0 | 2.0 | 0.0 | 3.0 | 0.0 | 0.0 | 0.0 | 0.0 | 4.0 | 0.0 | — | 0.0 |
| | 1.000 | 2.5 | 9.0 | 9.0 | 9.0 | 0.0 | 9.0 | 8.0 | 6.0 | 9.0 | 2.0 | — | 0.0 |
| 40 | .500 | 2.5 | 8.0 | 6.0 | 6.0 | 0.0 | 8.0 | 7.0 | 2.0 | 8.0 | 1.0 | — | 0.0 |

TABLE IV-continued
PRE-EMERGENCE TESTS - RATES IN KG/HA

| Compound of EXAMPLE | Rate | BA | BG | CH | FO | PN | WO | ST | MA | WM | SE | VL | BR |
|---|---|---|---|---|---|---|---|---|---|---|---|---|---|
| | .250 | 2.0 | 4.0 | 6.0 | 6.0 | 0.0 | 3.0 | 2.0 | 1.0 | 8.0 | 0.0 | — | 0.0 |
| | .125 | 0.5 | 2.0 | 3.0 | — | 0.0 | 0.0 | 2.0 | 1.0 | 2.0 | 0.0 | — | 0.0 |
| | 1.000 | 9.0 | 9.0 | 9.0 | 9.0 | 4.0 | 9.0 | 9.0 | 5.0 | 8.0 | 9.0 | — | 7.0 |
| 41 | .500 | 6.5 | 8.0 | 9.0 | 9.0 | 4.0 | 7.0 | 7.0 | 5.0 | 8.0 | — | — | 6.0 |
| | .250 | 4.0 | 8.0 | 6.0 | 6.0 | 2.0 | 4.0 | 7.0 | 2.0 | 8.0 | 0.0 | — | 2.0 |
| | .125 | 4.0 | 6.0 | 5.0 | 6.0 | 0.0 | 2.0 | 4.0 | 2.0 | 7.0 | 0.0 | — | 0.0 |
| | 1.000 | 6.0 | 7.0 | 8.0 | 9.0 | 0.0 | 8.0 | 9.0 | 3.0 | 8.0 | 0.0 | — | 0.0 |
| 42 | .500 | 2.0 | 8.0 | 8.0 | 9.0 | 0.0 | 2.0 | 9.0 | 5.0 | 8.0 | 0.0 | — | 0.0 |
| | .250 | 2.0 | 2.0 | 7.0 | 6.0 | 0.0 | 1.0 | 7.0 | 0.0 | 4.0 | 0.0 | — | 0.0 |
| | .125 | 0.0 | 0.0 | 0.0 | 5.0 | 0.0 | 0.0 | 0.0 | 0.0 | 0.0 | 0.0 | — | 0.0 |
| | 1.000 | 8.0 | 8.0 | 7.0 | 9.0 | 4.0 | 7.0 | 9.0 | 2.0 | 9.0 | 2.0 | — | 4.0 |
| 43 | .500 | 7.0 | 6.0 | 8.0 | 9.0 | 2.0 | 4.0 | 9.0 | 6.0 | 8.0 | 0.0 | — | 2.0 |
| | .250 | 2.5 | 0.0 | 2.0 | 7.0 | 0.0 | 1.0 | 8.0 | 0.0 | 8.0 | 0.0 | — | 0.0 |
| | .125 | 1.0 | 0.0 | 0.0 | 6.0 | 0.0 | 0.0 | 2.0 | 0.0 | 0.0 | 0.0 | — | 0.0 |
| | 1.000 | 9.0 | 9.0 | 9.0 | 9.0 | 9.0 | 9.0 | 9.0 | 5.0 | 9.0 | 0.0 | — | 9.0 |
| 44 | .500 | 4.5 | 7.0 | 9.0 | 9.0 | 7.0 | 4.0 | 9.0 | 6.0 | 9.0 | 0.0 | — | 7.0 |
| | .250 | 0.5 | 0.0 | 8.0 | 2.0 | 2.0 | 2.0 | 9.0 | 0.0 | 8.0 | 0.0 | — | 4.0 |
| | .125 | 0.0 | 0.0 | 0.0 | 0.0 | 2.0 | 0.0 | 4.0 | 0.0 | 0.0 | 0.0 | — | 2.0 |
| | 1.000 | 9.0 | 9.0 | 9.0 | 9.0 | 9.0 | 9.0 | 9.0 | 8.0 | 8.0 | 4.0 | — | 4.0 |
| 45 | .500 | 9.0 | 9.0 | 8.0 | 9.0 | 6.0 | 8.0 | 9.0 | 8.0 | 8.0 | 1.0 | — | 4.0 |
| | .250 | 8.0 | 8.0 | 8.0 | 9.0 | 2.0 | 5.0 | 9.0 | 2.0 | 7.0 | 0.0 | — | 2.0 |
| | .125 | 4.0 | 5.0 | 3.0 | 7.0 | 2.0 | 4.0 | 9.0 | 0.0 | 5.0 | 0.0 | — | 1.0 |
| | 1.000 | 9.0 | 9.0 | 9.0 | 9.0 | 9.0 | 8.0 | 9.0 | 8.0 | 8.0 | 8.0 | — | 9.0 |
| 46 | .500 | 9.0 | 9.0 | 9.0 | 9.0 | 9.0 | 7.0 | 9.0 | 7.0 | 8.0 | 3.0 | — | 7.0 |
| | .250 | 7.7 | 9.0 | 8.0 | 9.0 | 4.5 | 4.0 | 9.0 | 5.0 | 8.0 | 1.0 | — | 5.5 |
| | .125 | 6.7 | 4.0 | 6.0 | 8.0 | 3.0 | 2.0 | 9.0 | 4.0 | 7.0 | 0.0 | — | 2.0 |
| | 1.000 | 6.5 | 9.0 | 9.0 | 8.0 | 0.0 | 6.0 | 9.0 | 0.0 | 8.0 | 0.0 | — | 0.0 |
| 48 | .500 | 3.5 | 8.0 | 2.0 | 7.0 | 0.0 | 3.0 | 7.0 | 0.0 | 7.0 | 0.0 | — | 0.0 |
| | .250 | 2.0 | 0.0 | 0.0 | 5.0 | 0.0 | 0.0 | 7.0 | 0.0 | 7.0 | 0.0 | — | 0.0 |
| | .125 | 0.0 | 0.0 | 0.0 | 0.0 | 0.0 | 0.0 | 0.0 | 0.0 | 2.0 | 0.0 | — | 0.0 |
| | 1.000 | 0.0 | 0.0 | 0.0 | 0.0 | — | 0.0 | — | 0.0 | 0.0 | — | — | — |
| 49 | .500 | 0.0 | 0.0 | 0.0 | 0.0 | — | 0.0 | — | 0.0 | 0.0 | — | — | — |
| | .250 | 0.0 | 0.0 | 0.0 | 0.0 | — | 0.0 | — | 0.0 | 0.0 | — | — | — |
| | .125 | 0.0 | 0.0 | 0.0 | 0.0 | — | 0.0 | — | 0.0 | 0.0 | — | — | — |
| 50 | .500 | 9.0 | 9.0 | 9.0 | 9.0 | — | 7.0 | — | 5.0 | 9.0 | — | — | — |
| | .250 | 6.0 | 6.0 | 5.0 | 9.0 | — | 5.0 | — | 2.0 | 9.0 | — | — | — |
| | .125 | 5.0 | 4.0 | 5.0 | 6.0 | — | 3.0 | — | 0.0 | 9.0 | — | — | — |
| | 1.000 | 3.5 | 9.0 | 9.0 | 9.0 | 9.0 | 9.0 | 6.0 | 5.0 | 9.0 | 0.0 | — | 0.0 |
| 51 | .500 | 5.0 | 6.0 | 9.0 | 7.0 | 9.0 | 7.0 | 9.0 | 5.0 | 8.0 | 0.0 | — | 0.0 |
| | .250 | 2.0 | 6.0 | 9.0 | 9.0 | 4.0 | 6.0 | 9.0 | 1.0 | 7.0 | 0.0 | — | 0.0 |
| | .125 | 1.5 | 3.0 | 5.0 | 4.0 | 2.0 | 4.0 | 0.0 | 1.0 | 5.0 | 0.0 | — | 0.0 |
| | 1.000 | 8.0 | 5.0 | 9.0 | 9.0 | — | 2.0 | — | 0.0 | 9.0 | — | — | — |
| 52 | .500 | 2.0 | 6.0 | 5.0 | 6.0 | — | 0.0 | — | 0.0 | 8.0 | — | — | — |
| | .250 | 0.0 | 0.0 | 0.0 | 5.0 | — | 0.0 | — | 0.0 | 8.0 | — | — | — |
| | .125 | 0.0 | 0.0 | 0.0 | 0.0 | — | 0.0 | — | 0.0 | 4.0 | — | — | — |
| | 1.000 | 9.0 | — | — | — | 9.0 | — | 8.0 | — | — | — | — | 9.0 |
| 53 | .500 | 2.0 | — | — | — | 3.0 | — | 8.0 | — | — | — | — | 6.0 |
| | .250 | 0.0 | — | — | — | 0.0 | — | 0.0 | — | — | — | — | 0.0 |
| | .125 | 0.0 | — | — | — | 0.0 | — | 0.0 | — | — | — | — | 0.0 |
| | 1.000 | 0.0 | — | — | — | 9.0 | — | 2.0 | — | — | — | — | 9.0 |
| 54 | .500 | 0.0 | — | — | — | 2.0 | — | 0.0 | — | — | — | — | 4.0 |
| | .250 | 0.0 | — | — | — | 0.0 | — | 0.0 | — | — | — | — | 0.0 |
| | .125 | 0.0 | — | — | — | 0.0 | — | 0.0 | — | — | — | — | 0.0 |
| | 1.000 | 9.0 | 5.0 | 9.0 | 7.0 | 6.0 | 5.0 | 9.0 | 8.0 | 9.0 | — | — | 9.0 |
| 55 | .500 | 4.0 | 1.0 | 4.0 | 1.0 | 6.0 | 4.0 | 4.0 | 2.0 | 9.0 | — | — | 7.0 |
| | .250 | 0.0 | 0.0 | 3.0 | 0.0 | 2.0 | 0.0 | 0.0 | 2.0 | 9.0 | — | — | 4.0 |
| | .125 | 0.0 | 0.0 | 0.0 | 0.0 | 0.0 | 0.0 | 0.0 | 2.0 | 8.0 | — | — | 0.0 |
| | 1.000 | 4.3 | 7.0 | 9.0 | 6.0 | 9.0 | 9.0 | 3.5 | 2.0 | 8.5 | 6.5 | 6.0 | 8.5 |
| 56 | .500 | 2.3 | 5.0 | 6.0 | 2.0 | 6.5 | 5.0 | 0.5 | 2.0 | 8.0 | 4.0 | — | 7.0 |
| | .250 | 1.3 | 4.0 | 3.0 | 0.0 | 5.0 | 1.0 | 0.0 | 0.0 | 8.0 | 1.0 | — | 2.0 |
| | .125 | 0.7 | 0.0 | 2.0 | 0.0 | 3.5 | 0.0 | 0.0 | 0.0 | 7.0 | 1.0 | — | 2.0 |
| | 1.000 | 5.3 | 8.0 | 7.0 | 3.0 | 5.0 | 9.0 | 7.5 | 3.0 | 9.0 | 3.0 | — | 3.0 |
| 57 | .500 | 3.7 | 6.0 | 6.0 | 0.0 | 1.0 | 5.0 | 6.0 | 4.0 | 9.0 | 2.0 | — | 4.0 |
| | .250 | 0.7 | 1.0 | 5.0 | 0.0 | 1.0 | 1.0 | 1.0 | 0.0 | 7.0 | 1.0 | — | 1.0 |
| | .125 | 0.0 | 0.0 | 4.0 | 0.0 | 0.0 | 0.0 | 1.0 | 0.0 | 7.0 | 0.0 | — | 2.0 |
| | 1.000 | 2.0 | 5.0 | 6.0 | 5.0 | 2.0 | 4.0 | 2.0 | 0.0 | 9.0 | 5.5 | — | 3.0 |
| 58 | .500 | 0.7 | 3.0 | 6.0 | 1.0 | 2.0 | 0.0 | 0.5 | 0.0 | 9.0 | 3.0 | — | 2.0 |
| | .250 | 0.7 | 0.0 | 0.0 | 0.0 | 2.0 | 0.0 | 0.0 | 0.0 | 9.0 | 0.0 | — | 1.0 |
| | .125 | 0.0 | 0.0 | 0.0 | 0.0 | 1.0 | 0.0 | 0.0 | 0.0 | 7.0 | 0.0 | — | 0.0 |
| | 1.000 | 5.3 | 9.0 | 9.0 | 6.5 | 6.0 | 7.0 | 4.5 | 6.0 | 8.0 | 4.5 | 6.0 | 4.5 |
| 59 | .500 | 5.0 | 8.0 | 9.0 | — | 4.0 | 7.0 | 4.5 | 6.0 | 8.0 | 4.5 | — | 4.0 |
| | .250 | 3.3 | 4.0 | 8.0 | 6.0 | 3.5 | 6.0 | 0.0 | 3.0 | 8.0 | 1.0 | — | 3.5 |
| | .125 | 1.3 | 4.0 | — | 4.0 | 0.0 | 4.0 | 0.0 | 4.0 | 6.0 | 0.0 | — | 0.0 |
| | 1.000 | 7.7 | 9.0 | 9.0 | 9.0 | 6.0 | 7.0 | 7.5 | 6.0 | 8.0 | 6.5 | — | 8.0 |
| 60 | .500 | 5.0 | 6.0 | 7.0 | 6.0 | 4.5 | 7.0 | 4.5 | 5.0 | 8.0 | 5.0 | — | 4.5 |
| | .250 | 4.0 | 5.0 | 7.0 | 5.0 | 4.5 | 5.0 | 1.0 | 4.0 | 7.0 | 3.0 | — | 2.0 |
| | .125 | 2.3 | 3.0 | 6.0 | 4.0 | 2.0 | 4.0 | 0.0 | 4.0 | 6.0 | 1.0 | — | 1.0 |
| | 1.000 | 6.5 | 6.0 | 8.0 | 9.0 | 7.0 | 5.0 | 9.0 | 5.0 | 8.0 | 4.0 | — | 6.0 |
| 61 | .500 | 5.5 | 6.0 | 6.0 | 6.0 | 2.0 | 3.0 | 9.0 | 4.0 | 8.0 | 2.0 | — | 6.0 |

TABLE IV-continued
PRE-EMERGENCE TESTS - RATES IN KG/HA

| Compound of EXAMPLE | Rate | BA | BG | CH | FO | PN | WO | ST | MA | WM | SE | VL | BR |
|---|---|---|---|---|---|---|---|---|---|---|---|---|---|
|  | .250 | 2.0 | 2.0 | 4.0 | 3.0 | 2.0 | 1.0 | 2.0 | 0.0 | 8.0 | 0.0 | — | 2.0 |
|  | .125 | 2.5 | 3.0 | 4.0 | 3.0 | 0.0 | 0.0 | 0.0 | 1.0 | 7.0 | 0.0 | — | 0.0 |
|  | 1.000 | 7.0 | 6.0 | 7.0 | 7.0 | 4.0 | 5.0 | 9.0 | 2.0 | 9.0 | 2.0 | — | 6.0 |
| 62 | .500 | 3.0 | 4.0 | 3.0 | 6.0 | 2.0 | 1.0 | 2.0 | 2.0 | 9.0 | 0.0 | — | 2.0 |
|  | .250 | 1.5 | 1.0 | 1.0 | 2.0 | 2.0 | 0.0 | 0.0 | 1.0 | 9.0 | 0.0 | — | 2.0 |
|  | .125 | 0.0 | 0.0 | 0.0 | 0.0 | 0.0 | 0.0 | 0.0 | 0.0 | 1.0 | 0.0 | — | 0.0 |
|  | 1.000 | 0.5 | 2.0 | 4.0 | 4.0 | 2.0 | 4.0 | 0.0 | 2.0 | 8.0 | 0.0 | — | 6.0 |
| 63 | .500 | 1.5 | 0.0 | 4.0 | 4.0 | 2.0 | 2.0 | 0.0 | 2.0 | 8.0 | 0.0 | — | 4.0 |
|  | .250 | 0.5 | 0.0 | 3.0 | 4.0 | 1.0 | 0.0 | 0.0 | 0.0 | 7.0 | 0.0 | — | 2.0 |
|  | .125 | 0.0 | 0.0 | 3.0 | 3.0 | 1.0 | 0.0 | 0.0 | 0.0 | 4.0 | 0.0 | — | 2.0 |
|  | 1.000 | 2.5 | 6.0 | 6.0 | 5.0 | 1.0 | 5.0 | 0.0 | 6.0 | 9.0 | 0.0 | — | 6.0 |
| 64 | .500 | 1.0 | 4.0 | 5.0 | 1.0 | 0.0 | 4.0 | 0.0 | 0.0 | 8.0 | 0.0 | — | 1.0 |
|  | .250 | 1.5 | 3.0 | 5.0 | 0.0 | 0.0 | 1.0 | 0.0 | 0.0 | 8.0 | 0.0 | — | 1.0 |
|  | .125 | 1.5 | 0.0 | 2.0 | 0.0 | 0.0 | 0.0 | 0.0 | 0.0 | 8.0 | 0.0 | — | 1.0 |
|  | 1.000 | 6.5 | 9.0 | 9.0 | 6.0 | 4.0 | 8.0 | 9.0 | 5.0 | 8.0 | 4.0 | — | 4.0 |
| 65 | .500 | 4.0 | 7.0 | 9.0 | 6.0 | 2.0 | 7.0 | 8.0 | 5.0 | 8.0 | 1.0 | — | 4.0 |
|  | .250 | 3.5 | — | 6.0 | 4.0 | 0.0 | 4.0 | 6.0 | 3.0 | 8.0 | 0.0 | — | 2.0 |
|  | .125 | 2.5 | 4.0 | 5.0 | 2.0 | 0.0 | 2.0 | 0.0 | 3.0 | 8.0 | 4.0 | — | 0.0 |
|  | 1.000 | 3.0 | 2.0 | 2.0 | 2.0 | 0.0 | 0.0 | 4.0 | 0.0 | 7.0 | 0.0 | — | 0.0 |
| 66 | .500 | 2.0 | 0.0 | 0.0 | 0.0 | 0.0 | 0.0 | 2.0 | 0.0 | 0.0 | 0.0 | — | 0.0 |
|  | .250 | 0.0 | 0.0 | 0.0 | 0.0 | 0.0 | 0.0 | 1.0 | 0.0 | 0.0 | 0.0 | — | 0.0 |
|  | .125 | 0.0 | 0.0 | 0.0 | 0.0 | 0.0 | 0.0 | 1.0 | 0.0 | 0.0 | 0.0 | — | 0.0 |
|  | 1.000 | 8.3 | 9.0 | 9.0 | 8.0 | 9.0 | 9.0 | 9.0 | 5.0 | 9.0 | 6.5 | — | 8.0 |
| 67 | .500 | 3.7 | 9.0 | 9.0 | 7.0 | 8.5 | 7.0 | 7.0 | 4.0 | 9.0 | 3.0 | — | 3.0 |
|  | .250 | 1.0 | 6.0 | 9.0 | 7.0 | 2.0 | 6.0 | 0.5 | 0.0 | 8.0 | 0.0 | — | 1.0 |
|  | .125 | 0.0 | 0.0 | 6.0 | 0.0 | 2.0 | 5.0 | 0.0 | 0.0 | 6.0 | 0.0 | — | 0.0 |

EXAMPLE 69
Rice Tolerance to Post-Transplanting Applications

The selectivity of the compounds of the invention is exemplified by the following tests in which two-ten-day old rice seedlings (cv. S-201) are transplanted into a 32 oz plastic container with a diameter of 10.5 cm containing 700 grams of a slit loam soil. After planting the containers are flooded and the water level is maintained at 0.5 to 3.0 cm above the soil surface. Three to seven days after transplanting, the flooded soil surface of the cups are treated with the selected aqueous acetone solution containing test compound in sufficient quantity to provide the equivalent of about 0.063 to 2.0 kg per hectare of test compound per cup. The treated cups are then placed on greenhouse benches, watered such that water level is maintained as stated above, and cared for in accordance with conventional greenhouse procedures. Three to five weeks after treatment, the tests are terminated and each cup is examined and rated according to the rating system provided in Example 68. The data obtained are reported in Table V below.

TABLE V
Rice tolerance to post-transplanting applications

| Compound of Example | Rate kg/ha | | | |
|---|---|---|---|---|
|  | 1.0 | 0.5 | 0.25 | 0.125 |
| 1 | — | — | — | — |
| 2 | 4.9 | 3.5 | 2.5 | 1.8 |
| 3 | 2.0 | 2.0 | 1.0 | 3.0 |
| 4 (erythro) | 0.0 | 0.0 | 0.0 | 0.0 |
| 5 | 7.0 | 7.0 | 3.0 | 2.0 |
| 6 | 0.0 | 0.0 | 0.0 | — |
| 7 | 0.0 | 0.0 | 0.0 | — |
| 8 | 0.0 | 0.0 | 0.0 | — |
| 9 | 0.5 | 0.5 | 0.0 | 0.0 |
| 10 | 2.3 | 1.0 | 0.5 | 0.5 |
| 11 | 0.0 | 0.0 | 0.0 | 0.0 |
| 12 | 1.0 | 0.0 | 0.0 | 0.0 |
| 13 | 4.0 | 2.0 | 1.0 | 0.0 |
| 14 | 3.5 | 3.0 | 6.0 | 2.0 |
| 15 | 4.0 | 2.0 | 1.0 | 1.0 |
| 16 | 3.0 | 1.0 | 0.0 | 0.0 |
| 17 | 3.0 | 1.0 | 0.0 | 0.0 |
| 18 | 1.0 | 2.0 | 0.0 | 1.0 |
| 19 | — | — | — | — |
| 20 | 6.0 | 0.0 | 0.0 | 0.0 |
| 23 | 4.0 | 0.5 | 0.0 | 0.0 |
| 24 | 3.0 | 3.0 | 2.0 | 1.0 |
| 25 | 2.5 | 0.8 | 0.0 | 0.0 |
| 26 | 1.5 | 0.5 | 0.2 | 0.0 |
| 27 | 0.0 | 0.0 | 0.0 | — |
| 28 | 1.3 | 0.5 | 0.3 | 0.5 |
| 29 | — | — | — | — |
| 30 | 0.5 | 0.5 | 0.0 | 0.0 |
| 31 | 4.0 | 3.5 | 1.0 | 1.0 |
| 33 | 6.3 | 1.0 | 0.3 | 0.3 |
| 34 | 6.0 | 3.0 | 2.0 | 0.0 |
| 35 | 0.0 | 0.0 | 0.0 | 0.0 |
| 36 | 3.0 | 1.0 | 0.0 | 0.0 |
| 37 | 3.0 | 2.0 | 3.0 | 1.0 |
| 38 | 1.0 | 0.0 | 0.0 | 0.0 |
| 39 | 0.0 | 0.0 | 0.0 | 0.0 |
| 40 | 2.0 | 2.0 | 1.0 | 0.0 |
| 41 | — | — | — | — |
| 42 | 1.0 | 1.0 | 0.0 | 0.0 |
| 43 | 0.0 | 0.0 | 0.0 | 0.0 |
| 44 | 8.0 | 1.0 | 0.0 | 0.0 |
| 45 | 8.0 | 4.0 | 0.0 | 0.0 |
| 46 | 4.0 | 4.0 | 3.0 | 1.0 |
| 53 | 0.0 | 0.0 | 0.0 | — |
| 54 | 0.0 | 0.0 | 0.0 | — |
| 55 | 0.0 | 0.0 | 0.0 | — |
| 56 | 1.0 | 0.5 | 0.0 | 0.0 |
| 57 | 2.0 | 1.0 | 0.0 | 0.0 |
| 58 | 0.5 | 0.5 | 0.5 | 0.0 |
| 59 | 1.0 | 0.0 | 0.0 | 0.0 |
| 60 | 5.0 | 2.0 | 1.0 | 1.0 |
| 61 | 1.0 | 1.0 | 1.0 | 1.0 |
| 62 | 1.0 | 0.0 | 0.0 | 0.0 |
| 63 | 0.0 | 0.0 | 0.0 | 0.0 |
| 64 | 0.0 | 0.0 | 0.0 | 0.0 |
| 65 | — | — | — | — |
| 66 | 3.0 | 0.0 | 0.0 | 0.0 |

EXAMPLE 70

Postemergence Herbicidal Activity and Selectivity in Transplanted and Direct-Seeded Rice The postemergence herbicidal activity and rice selectivity of some of the compounds of the present invention is demonstrated by the following tests, wherein a variety of monocotyledonous and dicotyledonous plants are treated with test compounds dispersed in aqueous acetone mixtures. In the tests, seedling plants are grown in separate cups for about two weeks. The cups are then sprayed with the selected aqueous acetone solution containing test compound in sufficient quantity to provide the equivalent of about 0.063 kg to 2 kg per hectare of test compound per cup. These solutions also contained 0.5% of a spreader activator such as an alkylaryl polyoxyethylene glycol plus free fatty acid and isopropanol. After spraying, the plants are placed on greenhouse benches and are cared for in the usual manner, commensurate with conventional greenhouse practices. Three to five weeks after treatment, the seedling plants are examined and rated according to the rating system set forth in Example 68. The data obtained are reported in Table VI below.

| Abbreviation | Plants Common Name | Scientific Name |
|---|---|---|
| BA | Barnyardgrass | *Echinochloa crus-galli* (L.) Beauv. |
| PN | Purple Nutsedge | *Cyperus rotundus* L. |
| RR | Red Rice | *Oryza sativa* L. (weed) |
| ST | Sprangletop | *Leptochloa filiformis* (LAM.) Beauv. |
| SE | Sesbania | *Sesbania exaltata* (Raf.) Rydb. ex. A. W. Hill |
| BR | Bulrush | *Scirpus* spp. |
| RL | Rice CV. Labelle | *Oryza sativa* L. 'Labelle' |
| RK | Rice CV. Koshi-Hikari | *Oryza sativa* L. ',Koshi-Hikari' |
| RN | Rice CV. Nato | *Oryza sativa* L. 'Nato' |

TABLE VI

Postemergence herbicidal activity and selectivity in rice of compounds having the structure

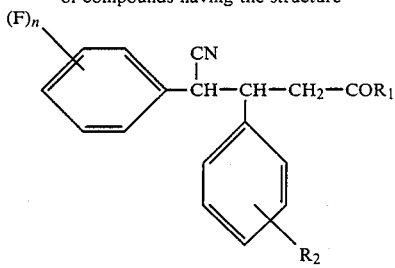

| Compound ERYTHRO-/THREO* | R₁ | R₂ | (F)ₙ | RATE | BA | PN | RR | ST | SE | BR | Rice RL | RK | RN |
|---|---|---|---|---|---|---|---|---|---|---|---|---|---|
| 57/43 | OCH$_3$ | 3-F | 4-F | 1.000 | 8.0 | 2.0 | 6.0 | 9.0 | 8.0 | 7.0 | 7.0 | 4.0 | 5.0 |
| | | | | .500 | 7.0 | 0.0 | 2.0 | 9.0 | 9.0 | 6.0 | 3.0 | 3.0 | 2.0 |
| | | | | .250 | 4.0 | 0.0 | 2.0 | 6.0 | 9.0 | 4.0 | 2.0 | 3.0 | 0.0 |
| | | | | .125 | 4.0 | 0.0 | 2.0 | 8.0 | 2.0 | 4.0 | 2.0 | 2.0 | 1.0 |
| 58/42 | ONa | 3-F | 4-F | 1.000 | 6.0 | 9.0 | 4.0 | 7.0 | 9.0 | 4.0 | 7.0 | 6.0 | 4.0 |
| | | | | .500 | 2.0 | 9.0 | 6.0 | 2.0 | 6.0 | 7.0 | 4.0 | 8.0 | 3.0 |
| | | | | .250 | 2.0 | 9.0 | 4.0 | 0.0 | 0.0 | 7.0 | 2.0 | 2.0 | 2.0 |
| | | | | .125 | 2.0 | 7.0 | 2.0 | 0.0 | 0.0 | 4.0 | 1.0 | 6.0 | 2.0 |
| 62/38 | OH | 3-F | 4-F | 1.000 | 9.0 | 8.0 | 2.0 | 8.0 | 4.0 | 7.0 | 3.0 | 6.0 | 3.0 |
| | | | | .500 | 6.0 | 9.0 | 2.0 | 7.0 | 2.0 | 7.0 | 2.0 | 2.0 | 2.0 |
| | | | | .250 | — | 6.0 | 0.0 | 2.0 | 2.0 | 4.0 | 2.0 | 4.0 | 2.0 |
| | | | | .125 | 0.0 | 6.0 | 0.0 | 0.0 | 0.0 | 4.0 | 1.0 | 2.0 | 1.0 |
| 56/44 | OCH$_3$ | 3-Cl | 3,4-F$_2$ | .500 | 9.0 | 2.0 | 6.0 | 9.0 | 8.0 | 7.0 | 2.0 | 2.0 | 1.0 |
| | | | | .250 | 7.0 | 4.0 | 4.0 | 8.0 | 1.0 | 5.0 | 1.0 | 2.0 | 1.0 |
| | | | | .125 | 2.0 | 4.0 | 1.0 | 7.0 | 0.0 | 6.0 | 0.0 | 1.0 | 0.0 |
| 54/46 | ONa | 3-Cl | 3,4-F$_2$ | .500 | 7.0 | 4.0 | 6.0 | 9.0 | 5.0 | 5.0 | 4.0 | 2.0 | 2.0 |
| | | | | .250 | 6.0 | 2.0 | 3.0 | 6.0 | 3.0 | 5.0 | 2.0 | 1.0 | 1.0 |
| | | | | .125 | 2.0 | 2.0 | 1.0 | 4.0 | 1.0 | 4.0 | 2.0 | 1.0 | 0.0 |
| 59/41 | OH | 3-Cl | 3,4-F$_2$ | 1.000 | 8.0 | 6.0 | 7.0 | 8.0 | 8.0 | 8.0 | 4.0 | 4.0 | 3.0 |
| | | | | .500 | 9.0 | 6.0 | 8.0 | 9.0 | 8.0 | 6.0 | 3.0 | 2.0 | 2.0 |
| | | | | .250 | 5.0 | 4.0 | 2.0 | 6.0 | 3.0 | 6.0 | 1.0 | 2.0 | 0.0 |
| | | | | .125 | 4.0 | 2.0 | 2.0 | 6.0 | 1.0 | 6.0 | 0.0 | 1.0 | 0.0 |

EXAMPLE 71

Preemergence Herbicidal Activity and Selectivity in Wheat and Barley

The preemergence herbicidal activity and selectivity of some of the compounds of the present invention is exemplified by the following tests in which the seeds or propagating organs of a variety of monocotyledonous and dicotyledonous plants are separately mixed with potting soil and planted on top of approximately 2.5 cm of soil in separate cups. After planting, the cups are sprayed with the selected aqueous acetone solution containing test compound in sufficient quantity to provide the equivalent of about 0.063 kg to 2.0 kg per hectare of test compound per cup. The treated cups are then placed on greenhouse benches, watered and cared for in accordance with conventional greenhouse procedures. Three to five weeks after treatment, the tests are terminated and each cup is examined and rated according to the rating system provided in Example 68. The data obtained are reported in Table VII below.

Crop varieties

**Cultivated varieties of barley (*Hordeum vulgare* L.)**

| Abbreviation | Cultivated variety |
|---|---|
| LARK | Larker |
| AURA | Aura |
| BONAN | Bonanza |

**Cultivated varieties of wheat (*Triticum aestivum* L.)**

| | |
|---|---|
| FENM | Fenman |
| ERA | Era |
| ANZA | Anza |

Weed Species

| Abbreviation | Common Name | Scientific Name |
|---|---|---|
| BG | Blackgrass | *Alopecurus myosuroides* Huds |
| DB | Downy Brome | *Bromus tectorum.* L. |
| RC | Reed Canarygrass | *Phalaris arundinacea* L. |
| CH | Cheat | *Bromus secalinus* L. |
| LC | Large Crabgrass | *Digitaria sanguinalis* (L)Beauv |
| FO | Green Foxtail | *Setaria viridis* (L)Beauv. |
| WO | Wild Oats | *Avena fatua* L. |
| RG | Ryegrass | *Lolium perenne* L. |
| MA | Matricaria | *Matricaria* spp. |
| WM | Wild Mustard | *Sinapis arvensis* L. |

TABLE VII
Preemergence herbicidal activity and selectivity in wheat and barley of compounds having the structure
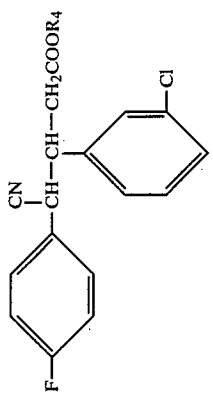
| ERYTHRO/THREO | R4 | RATE | BG | DB | RC | CH | LC | FO | WO | RG | MA | WM | LARK | BARLEY AURA | BONAN | FENM | WHEAT ERA | ANZA |
|---|---|---|---|---|---|---|---|---|---|---|---|---|---|---|---|---|---|---|
| 27/73 | C2H5 | 1.000 | — | 7.0 | — | — | 9.0 | 9.0 | 8.0 | — | — | 9.0 | — | — | — | — | — | 0.0 |
|  |  | .500 | — | 3.5 | — | — | 9.0 | 9.0 | 6.5 | — | — | 8.5 | — | — | 3.0 | — | 3.0 | 0.0 |
|  |  | .250 | — | 0.0 | — | — | 9.0 | 9.0 | 3.0 | — | — | 3.0 | — | — | — | — | — | 0.0 |
|  |  | .125 | — | 0.0 | — | — | 9.0 | 9.0 | 0.0 | — | — | 0.0 | — | — | — | — | — | 0.0 |
| 57/43 | CH3 | 1.000 | 9.0 | 3.0 | 9.0 | 9.0 | 9.0 | 9.0 | 8.0 | 4.5 | 4.5 | 9.0 | 4.0 | 2.0 | 3.0 | 3.5 | 3.0 | 2.5 |
|  |  | .750 | 7.0 | — | 6.0 | 9.0 | 9.0 | 9.0 | 8.0 | 2.0 | 2.0 | 9.0 | — | 1.0 | 3.0 | 2.0 | — | 2.0 |
|  |  | .500 | 9.0 | 3.0 | 5.5 | 8.0 | 9.0 | 8.5 | 7.0 | 1.5 | 4.0 | 8.0 | 1.0 | 0.5 | 0.5 | 1.5 | 0.0 | 0.5 |
|  |  | .375 | 9.0 | 5.0 | 5.5 | 6.0 | 9.0 | 9.0 | 6.0 | 1.5 | 0.5 | 8.0 | 0.0 | 0.0 | 0.0 | 0.5 | 0.0 | 0.5 |
|  |  | .250 | 3.0 | 1.0 | 4.5 | 3.5 | 7.0 | 5.5 | 1.5 | 0.5 | 0.0 | 6.5 | 0.0 | 0.0 | 0.0 | 0.0 | 0.0 | 0.0 |
|  |  | .125 | 1.5 | 0.0 | 3.5 | 3.5 | 6.0 | 5.5 | 0.0 | 0.0 | 0.0 | 5.5 | 0.0 | 0.0 | 0.0 | 0.0 | 0.0 | 0.0 |
| 55/45 | H | 1.000 | 8.0 | 9.0 | 9.0 | 6.0 | 9.0 | 9.0 | 9.0 | 0.0 | 9.0 | 9.0 | 7.0 | 7.0 | 7.0 | 7.0 | 7.0 | 6.0 |
|  |  | .500 | 5.0 | 9.0 | 6.0 | 6.0 | 8.0 | 9.0 | 5.0 | 6.0 | 8.0 | 9.0 | 4.0 | 5.0 | 5.0 | 6.0 | 5.0 | 5.0 |
|  |  | .375 | 4.0 | 9.0 | 5.0 | 6.0 | 7.0 | 9.0 | 7.0 | 5.0 | 8.0 | 9.0 | 4.0 | 4.0 | 3.0 | 5.0 | 5.0 | 3.0 |
|  |  | .250 | 2.0 | 4.0 | 6.0 | 5.0 | 6.0 | 9.0 | 4.0 | 4.0 | 4.0 | 9.0 | 1.0 | 1.0 | 4.0 | 1.0 | 0.0 | 3.0 |
|  |  | .125 | 0.0 | 2.0 | 3.0 | 2.0 | 0.0 | 4.0 | 0.0 | 1.0 | 0.0 | 9.0 | 0.0 | 0.0 | 1.0 | 0.0 | 0.0 | 1.0 |
| 61/39 | Na | 1.000 | 5.0 | 3.0 | 6.0 | 9.0 | — | 7.0 | 5.0 | 3.0 | 8.0 | 9.0 | 6.0 | 7.0 | 7.0 | 6.0 | 4.0 | 5.0 |
|  |  | .500 | 1.0 | 2.0 | 6.0 | 4.0 | — | 1.0 | 4.0 | 2.0 | 2.0 | 9.0 | 4.0 | 3.0 | 6.0 | 3.0 | 3.0 | 5.0 |
|  |  | .375 | 0.0 | 1.0 | 6.0 | 5.0 | — | 0.0 | 3.0 | 1.0 | 0.0 | 9.0 | 3.0 | 4.0 | 4.0 | 5.0 | 3.0 | 4.0 |
|  |  | .250 | 0.0 | 0.0 | 6.0 | 3.0 | — | 0.0 | 3.0 | 0.0 | 2.0 | 9.0 | 3.0 | 1.0 | 2.0 | 3.0 | 1.0 | 0.0 |
|  |  | .125 | 0.0 | 0.0 | 4.0 | 0.0 | — | 0.0 | 0.0 | 0.0 | 0.0 | 8.0 | 2.0 | 1.0 | 1.0 | 3.0 | 1.0 | 0.0 |
| 60/40 | i-C3H7 | 1.000 | 7.0 | — | 9.0 | 8.0 | 9.0 | 9.0 | 8.0 | 3.0 | 3.0 | 8.0 | — | 2.0 | 1.0 | 2.0 | — | 3.0 |
|  |  | .750 | 5.0 | — | 9.0 | 8.0 | 8.0 | 9.0 | 6.0 | 2.0 | 2.0 | 8.0 | — | 1.0 | 0.0 | 2.0 | — | 1.0 |
|  |  | .500 | 8.0 | — | 4.0 | 8.0 | 7.0 | 9.0 | 6.0 | 2.0 | 5.0 | 8.0 | — | 1.0 | 0.0 | 1.0 | — | 1.0 |
|  |  | .375 | 4.0 | — | 7.0 | 6.0 | 7.0 | 6.0 | 2.0 | 1.0 | 0.0 | 7.0 | — | 0.0 | 0.0 | 0.0 | — | 0.0 |
|  |  | .250 | 2.0 | — | 2.0 | 0.0 | 2.0 | 1.0 | 4.0 | 0.0 | 0.0 | 4.0 | — | 0.0 | 0.0 | 0.0 | — | 1.0 |
|  |  | .125 | 0.0 | — | 0.0 | 0.0 | 0.0 | 0.0 | 0.0 | 0.0 | 0.0 | 0.0 | — | 0.0 | 0.0 | 0.0 | — | 0.0 |
| 57/43 | C2H5 | 1.000 | 8.0 | — | 8.0 | 7.0 | 8.0 | 9.0 | 7.0 | 2.0 | 2.0 | 9.0 | — | 3.0 | 2.0 | 4.0 | — | 3.0 |
|  |  | .750 | 8.0 | — | 7.0 | 8.0 | 8.0 | 9.0 | 8.0 | 2.0 | 2.0 | 9.0 | — | 3.0 | 2.0 | 3.0 | — | 3.0 |
|  |  | .500 | 6.0 | — | 3.0 | 8.0 | 8.0 | 9.0 | 4.0 | 1.0 | 6.0 | 8.0 | — | 1.0 | 1.0 | 2.0 | — | 3.0 |
|  |  | .375 | 5.0 | — | 4.0 | 2.0 | 7.0 | 9.0 | 3.0 | 0.0 | 4.0 | 8.0 | — | 0.0 | 0.0 | 0.0 | — | 1.0 |
|  |  | .250 | 0.0 | — | 0.0 | 2.0 | 6.0 | 7.0 | 1.0 | 0.0 | 4.0 | 8.0 | — | 0.0 | 0.0 | 0.0 | — | 1.0 |
|  |  | .125 | 0.0 | — | 0.0 | 0.0 | 0.0 | 6.0 | 0.0 | 0.0 | 0.0 | 0.0 | — | 0.0 | 0.0 | 0.0 | — | 0.0 |

EXAMPLES 72 and 73

In addition to the compounds described in Table I, other examples of 4-cyano-3-substituted-phenyl-4-fluorophenylbutyric acids that can be prepared by the procedures of Examples 2 and 4, are listed in Table VIII below.

TABLE VIII
4-Cyano-3-substituted phenyl-4-fluorophenylbutyric Acids

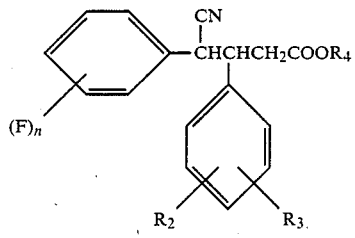

| | | | | Relative %* | | melting |
|---|---|---|---|---|---|---|
| Example | $R_2$ | $R_3$ | $(F)_n$ | erythro | threo | point (°C.) |
| 72 | p-OCH$_3$ | H | m-F | 61 | 39 | 131–153 |
| 73 | m-Cl | H | 3,4-diF | 98 | 2 | 79–84 |

*NMR(DMSO—d$_6$) δ C-4 CH doublet

EXAMPLES 74–136

Other examples of esters of 4-cyano-3-substituted-phenyl-4-fluorophenylbutyric acids that can be prepared as described in Examples 1 and 5 are listed in Table IX below.

TABLE IX
Esters of 4-Cyano-3-substituted phenyl-4-fluorophenylbutyric Acids

| | | | | | Relative %* | | |
|---|---|---|---|---|---|---|---|
| Example | $R_2$ | $R_3$ | $(F)_n$ | $R_4$ | erythro | threo | melting point (°C.) |
| 74 | 2-Cl | H | 3,4-diF | CH$_3$ | 0 | 100 | 71–72 |
| 75 | 2-Cl | H | 3,4-diF | CH$_3$ | 96 | 4 | colorless oil |
| 76 | 3-Cl | H | 2,5-diF | CH$_3$ | 50 | 50 | orange syrup |
| 77 | 3-Br | H | 3,4-diF | CH$_3$ | 57 | 43 | yellow syrup |
| 78 | 2-F | H | 3,4-diF | CH$_3$ | 54 | 46 | brown oil |
| 79 | 4-Br | H | 4-F | CH$_3$ | 60 | 40 | off-white semi-solid |
| 80 | 4-i-Pr | H | 3-F | CH$_3$ | 57 | 43 | amber oil |
| 81 | 2-F | H | 4-F | CH$_3$ | 52 | 48 | amber syrup |
| 82 | 3-CN | H | 4-F | CH$_3$ | 68 | 32 | off-white semi-solid |
| 83 | 4-OCH$_3$ | H | 3,4-diF | CH$_3$ | 60 | 40 | yellow syrup |
| 84 | 3-CH$_3$ | H | 3,4-diF | CH$_3$ | 55 | 45 | yellow syrup |
| 85 | 2-Cl | H | 3,4-diF | CH$_3$ | 59 | 41 | amber oil |
| 86 | 3-CF$_3$ | H | 3,4-diF | CH$_3$ | 58 | 42 | yellow syrup |
| 87 | 2,4-diF | | 3,4-diF | CH$_3$ | 55 | 45 | amber oil |
| 88 | 3,5-diF | | 4-F | CH$_3$ | 55 | 45 | yellow semi-solid |
| 89 | 4-NO$_2$ | H | 3,4-diF | CH$_3$ | 90 | 10 | 136–143 |
| 90 | 4-NO$_2$ | H | 3,4-diF | CH$_3$ | 8 | 92 | brown taffy |
| 91 | 4-Cl | H | 4-F | CH$_3$ | 59 | 41 | 90–102 |
| 92 | 2,4-diF | | 4-F | CH$_3$ | 54 | 46 | yellow oil |
| 93 | 3-OCF$_2$CF$_2$H | H | 3-F | CH$_3$ | 57 | 43 | brown oil |
| 94 | 4-SCH$_3$ | H | 3-F | CH$_3$ | 61 | 39 | pale yellow semi-solid |
| 95 | 4-OCF$_2$H | H | 4-F | CH$_3$ | 59 | 41 | amber oil |
| 96 | 4-SO$_2$CH$_3$ | H | 3-F | CH$_3$ | 59 | 41 | yellow oil |
| 97 | 3-Cl | H | 3,5-diF | CH$_3$ | 60 | 40 | light yellow syrup |
| 98 | 3-F | H | 3-Cl—4-F | CH$_3$ | 60 | 40 | amber oil |
| 99 | 3-Cl | H | 3-Cl—4-F | CH$_3$ | 59 | 41 | amber oil |
| 100 | 3-F | H | 3-F—4-OCH$_3$ | CH$_3$ | 55 | 45 | 96–106 |
| 101 | 2,6-diF | | 3-F | CH$_3$ | 67 | 33 | pale yellow semi-solid |
| 102 | 2,5-diF | | 3-F | CH$_3$ | 53 | 47 | orange semi-solid |
| 103 | 3-OCF$_2$H | | 3,4-diF | CH$_3$ | 57 | 43 | amber oil |
| 104 | 2-F—5-Br | | 3,4-diF | CH$_3$ | 53 | 46 | amber oil |
| 105 | 2-F—5-Cl | | 4-F | CH$_3$ | 51 | 49 | amber oil |
| 106 | 2-F—5-Cl | | 3,4-diF | CH$_3$ | 53 | 47 | amber semi-solid |
| 107 | 4-SCF$_2$H | H | 3-F | CH$_3$ | 60 | 40 | orange-brown semi-solid |
| 108 | 4-SO$_2$CF$_2$H | H | 3-F | CH$_3$ | 59 | 41 | yellow semi-solid |
| 109 | 3-OCF$_3$ | H | 4-F | CH$_3$ | 53 | 47 | amber oil |
| 110 | 3-I | H | 3,4-diF | CH$_3$ | 49 | 51 | amber viscous oil |

TABLE IX-continued
Esters of 4-Cyano-3-substituted phenyl-4-fluorophenylbutyric Acids

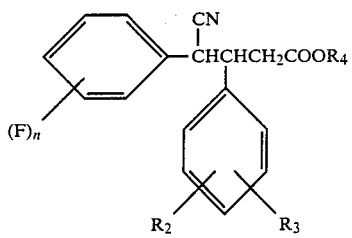

| Example | R$_2$ | R$_3$ | (F)$_n$ | R$_4$ | Relative %* erythro | threo | melting point (°C.) |
|---|---|---|---|---|---|---|---|
| 111 | pentaF | | 3-F | CH$_3$ | 58 | 42 | yellow semi-solid |
| 112 | 3-CF$_3$ | H | 3-F | CH$_3$ | 0 | 100 | 66-67 |
| 113 | 3-CF$_3$ | H | 3-F | CH$_3$ | 100 | 0 | 74-75.5 |
| 114 | 4-OCH$_3$ | H | 3-F | CH$_3$ | 56 | 44 | amber semi-solid |
| 115 | 4-OCH$_3$ | H | 4-F | CH$_3$ | 62 | 38 | amber oil |
| 116 | 3-OCH$_3$ | H | 3-F | CH$_3$ | 57 | 43 | amber semi-solid |
| 117 | 2-OCH$_3$ | H | 3-F | CH$_3$ | 48 | 52 | amber semi-solid |
| 118 | 4-OC$_2$H$_5$ | H | 3-F | CH$_3$ | 59 | 41 | amber semi-solid |
| 119 | 2-Br | H | 3-F | CH$_3$ | 33 | 67 | amber oil |
| 120 | 3,4-diOCH$_3$ | | 3-F | CH$_3$ | 63 | 37 | pale yellow semi-solid |
| 121 | 3-F—4-OCH$_3$ | | 3-F | CH$_3$ | 58 | 42 | 85-120 |
| 122 | 3,4-diOCH$_3$ | | 4-F | CH$_3$ | 62 | 38 | brown viscous oil |
| 123 | 4-OCH$_3$ | H | 3-F | CH$_3$ | 5 | 95 | water-white syrup |
| 124 | 4-OCH$_3$ | H | 3-F | CH$_3$ | 95 | 5 | 195.5-111 |
| 125 | 4-OCH$_3$ | H | 3-F | C$_2$H$_5$ | 61 | 39 | colorless oil |
| 126 | 4-OCH$_3$ | H | 3-F | n-C$_3$H$_7$ | 62 | 38 | colorless oil |
| 127 | 4-OCH$_3$ | H | 3-F | i-C$_3$H$_7$ | 58 | 42 | yellow semi-solid |
| 128 | 3-Cl—4-OMe | | 3-F | CH$_3$ | 58 | 42 | light brown semi-solid |
| 129 | 4-OSiMe$_2$t-Bu | | 3-F | CH$_3$ | 57 | 43 | yellow semi-solid |
| 130 | 4-CH$_3$ | H | 3-F | CH$_3$ | 59 | 41 | amber oil |
| 131 | 4-C$_2$H$_5$ | H | 3-F | CH$_3$ | 60 | 40 | amber viscous oil |
| 132 | 4-CN | H | 3-F | CH$_3$ | 62 | 38 | amber viscous oil |
| 133 | 4-OH | H | 3-F | CH$_3$ | 62 | 38 | off-white semi-solid |
| 134 | 4-OCOCH$_3$ | H | 3-F | CH$_3$ | 69 | 31 | amber oil |
| 135 | 4-CH$_2$OCH$_3$ | H | 3-F | CH$_3$ | 61 | 39 | amber oil |
| 136 | 4-OCOCH$_2$Cl | H | 3-F | CH$_3$ | 58 | 42 | off-white semi-solid |

*NMR(CDCl$_3$) δ C-4 CH doublet

EXAMPLE 137

Preparation of erythro- and threo-2-methoxyethyl 4-cyano-3-(m-fluorophenyl)-4-(p-fluorophenyl)butyrate

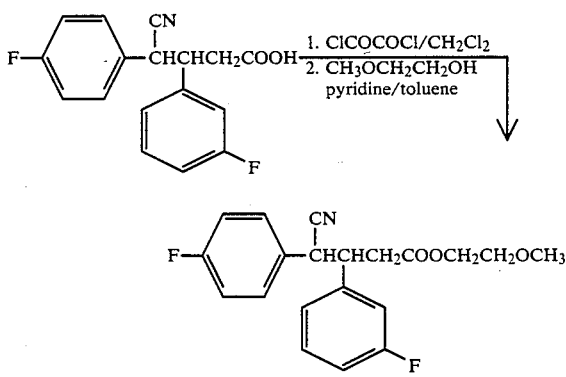

A solution of oxalyl chloride (4.5 g, 34 mmol) in 10 mL CH$_2$Cl$_2$ is added dropwise over a five-minute period to a solution of 4-cyano-3-(m-fluorophenyl)-4-(p-fluorophenyl)butyric acid (5.3 g, 17 mmol, erythro/threo=58/42) in 150 mL CH$_2$Cl$_2$. After the addition of one drop of N,N-dimethylformamide, the reaction mixture is stirred for three hours and is concentrated to yield a syrup. A toluene solution of the acid chloride (2.7 g, 8.4 mmol) is added over a 15-minute period to a solution of methoxyethanol (0.70 g, 9.2 mmol) and 5 mL pyridine at 0°. The resulting yellow suspension is warmed to room temperature and stirred overnight. After removing the solvent using a rotary evaporator, the resulting pale yellow liquid is partitioned between diethyl ether and water. The ether layer is washed twice with 10% HCl, twice with saturated aqueous sodium chloride and is stirred over magnesium sulfate. The filtered solution is concentrated to yield 2.0 g (67% yield) of an amber oil, identified as the title ester by the proton and carbon resonance spectra, mass spectrum and infrared spectrum. The isomer ratio is determined to be erythro/threo=62/38 based on the proton nmr spectrum (CDCl$_3$) as previously described. Other esters similarily prepared from the acid chloride using the appropriate alcohol are listed in Table X.

TABLE X
Esters of 4-Cyano-3-substituted phenyl-4-fluorophenylbutyric Acids

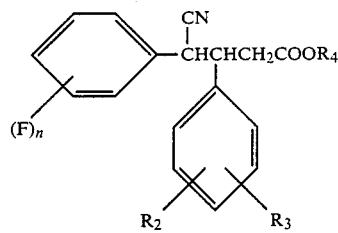

| Example | R$_2$ | R$_3$ | (F)$_n$ | R$_4$ | Relative %* erythro | threo | melting point (°C.) |
|---|---|---|---|---|---|---|---|
| 138 | 3-F | H | 4-F | Furfuryl | 61 | 39 | amber oil |
| 139 | 3-F | H | 4-F | Benzyl | 63 | 37 | off-white semi-solid |
| 140 | 4-OCH$_3$ | H | 3-F | CH$_2$CH$_2$OEt | 62 | 38 | colorless oil |
| 141 | 4-OCH$_3$ | H | 3-F | CH(CH$_3$)Ph | 61 | 31 | pale yellow oil |

EXAMPLE 142
Preemergence Herbicidal Activity

The preemergence herbicidal activity of the compounds of Examples 72–141 is exemplified using the procedure of Example 68. The data are reported in Table XI below.

TABLE XI
PRE-EMERGENCE TESTS - RATES IN KG/HA

| Compound of EXAMPLE | Rate | BA | BG | CH | FO | PN | WO | ST | MA | WM | SE | VL | BR |
|---|---|---|---|---|---|---|---|---|---|---|---|---|---|
| 72 | 1.000 | 0.0 | — | — | — | 4.0 | — | 9.0 | — | — | 2.0 | — | 2.0 |
|  | .500 | 0.0 | — | — | — | 4.0 | — | — | — | — | 2.0 | — | 4.0 |
|  | .250 | 0.0 | — | — | — | 0.0 | — | 0.0 | — | — | 0.0 | — | 0.0 |
|  | .125 | 0.0 | — | — | — | 0.0 | — | 0.0 | — | — | 0.0 | — | 0.0 |
| 74 | 4.000 | 9.0 | — | — | 9.0 | 9.0 | 9.0 | — | — | 9.0 | — | 9.0 | — |
| 75 | 4.000 | 0.0 | — | — | 0.0 | 0.0 | 0.0 | — | — | 0.0 | — | 1.0 | — |
| 76 | 1.000 | 8.0 | 9.0 | — | 8.0 | 0.0 | 8.0 | 7.0 | 0.0 | 8.0 | 1.0 | 9.0 | 0.0 |
|  | .500 | 3.0 | 9.0 | — | 5.0 | 0.0 | 4.0 | 3.0 | 0.0 | 8.0 | 0.0 | 6.0 | 0.0 |
|  | .250 | 1.0 | 9.0 | — | 5.0 | 0.0 | 0.0 | 1.0 | 0.0 | 7.0 | 0.0 | 3.0 | 0.0 |
|  | .125 | 0.0 | 0.0 | — | 2.0 | 0.0 | 0.0 | 0.0 | 0.0 | 3.0 | 0.0 | 0.0 | 0.0 |
| 77 | 1.000 | 9.0 | 9.0 | 9.0 | 9.0 | 2.0 | 9.0 | 9.0 | 7.0 | 9.0 | 2.0 | — | 2.0 |
|  | .500 | 8.5 | 9.0 | 9.0 | 8.0 | 0.0 | 9.0 | 9.0 | 6.0 | 9.0 | 0.0 | — | 0.0 |
|  | .250 | 6.0 | 7.0 | 9.0 | 7.0 | 0.0 | 6.0 | 6.0 | 3.0 | 9.0 | 0.0 | — | 0.0 |
|  | .125 | 1.0 | 0.0 | 9.0 | 0.0 | 0.0 | 8.0 | 2.0 | 0.0 | 9.0 | 0.0 | — | 0.0 |
| 78 | 1.000 | 8.3 | 9.0 | 9.0 | 9.0 | 8.0 | 9.0 | 9.0 | 5.0 | 9.0 | 6.3 | — | 8.0 |
|  | .500 | 7.0 | 9.0 | 9.0 | 9.0 | 5.8 | 9.0 | 9.0 | 3.0 | 9.0 | 5.0 | — | 8.0 |
|  | .250 | 5.3 | 9.0 | 9.0 | 9.0 | 4.3 | 6.0 | 8.5 | 0.0 | 9.0 | 3.3 | — | 7.0 |
|  | .125 | 3.5 | 4.0 | 9.0 | 9.0 | 2.0 | 5.0 | 6.5 | 0.0 | 9.0 | 0.7 | — | 6.0 |
| 79 | 1.000 | 7.7 | 9.0 | 9.0 | 9.0 | 4.0 | 0.0 | 9.0 | 2.0 | 9.0 | 1.0 | — | 1.0 |
|  | .500 | 5.3 | 9.0 | 9.0 | 9.0 | 2.7 | 6.0 | 9.0 | 0.0 | 9.0 | 0.0 | — | 0.0 |
|  | .250 | 1.3 | 9.0 | 9.0 | 9.0 | 0.7 | 0.0 | 7.0 | 0.0 | 8.0 | 0.0 | — | 0.0 |
|  | .125 | 0.0 | 6.0 | 9.0 | 9.0 | 0.7 | 0.0 | 2.0 | 0.0 | 8.0 | 0.0 | — | 0.0 |
| 80 | 4.000 | 0.0 | — | — | 0.0 | 1.0 | 0.0 | — | — | 6.0 | — | 0.0 | — |
|  | 1.000 | 0.0 | 0.0 | 0.0 | 0.0 | 0.0 | 0.0 | 0.0 | 0.0 | 0.0 | 0.0 | — | 0.0 |
|  | .500 | 0.0 | 0.0 | 0.0 | 0.0 | 0.0 | 0.0 | 0.0 | 0.0 | 0.0 | 0.0 | — | 0.0 |
|  | .250 | 0.0 | 0.0 | 0.0 | 0.0 | 0.0 | 0.0 | 0.0 | 0.0 | 0.0 | 0.0 | — | 0.0 |
|  | .125 | 0.0 | 0.0 | 0.0 | 0.0 | 0.0 | 0.0 | 0.0 | 0.0 | 0.0 | 0.0 | — | 0.0 |
| 81 | 1.000 | 4.2 | 9.0 | 9.0 | 8.0 | 3.8 | 8.0 | 4.5 | 2.0 | 9.0 | 1.8 | — | 1.8 |
|  | .500 | 4.3 | 7.0 | 9.0 | 9.0 | 4.3 | 7.0 | 9.0 | 0.0 | 8.0 | 3.0 | — | 3.5 |
|  | .375 | 3.0 | 7.0 | 8.0 | 9.0 | 6.0 | 7.0 | — | 0.0 | 8.0 | — | — | — |
|  | .250 | 2.0 | 6.0 | 8.0 | 3.0 | 3.7 | 4.0 | 4.0 | 0.0 | 8.0 | 2.0 | — | 1.0 |
|  | .125 | 0.7 | 0.0 | 8.0 | 0.0 | 0.0 | 0.0 | 2.0 | 0.0 | 7.0 | 0.0 | — | 0.5 |
| 82 | 1.000 | 2.0 | 0.0 | 4.0 | 0.0 | 0.0 | 4.0 | 0.0 | 0.0 | 9.0 | 0.0 | — | 0.0 |
|  | .500 | 0.0 | 0.0 | 0.0 | 0.0 | 0.0 | 4.0 | 0.0 | 0.0 | 7.0 | 0.0 | — | 0.0 |
|  | .250 | 0.0 | 0.0 | 0.0 | 0.0 | 0.0 | 3.0 | 0.0 | 0.0 | 0.0 | 0.0 | — | 0.0 |
|  | .125 | 0.0 | 0.0 | 0.0 | 0.0 | 0.0 | 2.0 | 0.0 | 0.0 | 0.0 | 0.0 | — | 0.0 |
| 83 | 1.000 | 9.0 | — | — | — | 8.0 | — | 9.0 | — | — | 8.0 | — | 7.5 |
|  | .500 | 8.0 | — | — | — | 7.5 | — | 9.0 | — | — | 2.5 | — | 7.0 |
|  | .250 | 6.3 | — | — | — | 7.5 | — | 7.7 | — | — | 0.0 | — | 6.5 |
|  | .125 | 3.3 | — | — | — | 5.5 | — | 4.7 | — | — | 0.0 | — | 5.0 |
| 84 | 1.000 | 7.0 | 9.0 | — | 9.0 | 6.0 | 6.0 | 9.0 | 9.0 | 9.0 | 0.0 | 7.0 | 4.0 |
|  | .500 | 2.0 | 8.0 | — | 9.0 | 2.0 | 6.0 | 9.0 | 0.0 | 9.0 | 0.0 | 7.0 | 2.0 |
|  | .250 | 2.0 | 7.0 | — | 9.0 | 0.0 | 0.0 | 8.0 | 0.0 | 9.0 | 0.0 | 7.0 | 2.0 |
|  | .125 | 0.0 | 8.0 | — | 9.0 | 0.0 | 2.0 | 7.0 | 0.0 | 9.0 | 0.0 | 6.0 | 0.0 |
| 85 | 1.000 | 6.5 | 9.0 | 9.0 | 9.0 | 4.0 | 9.0 | 9.0 | 5.0 | 9.0 | 4.0 | — | 7.0 |
|  | .500 | 5.0 | 9.0 | 9.0 | 9.0 | 2.0 | 6.0 | 9.0 | 0.0 | 9.0 | 2.0 | — | 2.0 |
|  | .250 | 1.0 | 6.0 | 9.0 | 9.0 | 0.0 | 4.0 | 8.0 | 0.0 | 8.0 | 0.0 | — | 0.0 |
|  | .125 | 1.0 | — | 9.0 | 9.0 | 0.0 | 0.0 | 4.0 | 0.0 | 0.0 | 0.0 | — | 0.0 |

TABLE XI-continued

PRE-EMERGENCE TESTS - RATES IN KG/HA

| Compound of EXAMPLE | Rate | BA | BG | CH | FO | PN | WO | ST | MA | WM | SE | VL | BR |
|---|---|---|---|---|---|---|---|---|---|---|---|---|---|
| 86 | 1.000 | 4.0 | 9.0 | — | 9.0 | 9.0 | 9.0 | 9.0 | 0.0 | 9.0 | 0.0 | 8.0 | 4.0 |
|  | .500 | 2.0 | 9.0 | — | 9.0 | 2.0 | 8.0 | 8.0 | 0.0 | 9.0 | 0.0 | 6.0 | 2.0 |
|  | .250 | 0.0 | 9.0 | — | 8.0 | 0.0 | 5.0 | 2.0 | 0.0 | 8.0 | 0.0 | 3.0 | 0.0 |
|  | .125 | 0.0 | 8.0 | — | 8.0 | 0.0 | 0.0 | 0.0 | 0.0 | 7.0 | 0.0 | 0.0 | 0.0 |
| 87 | 1.000 | 9.0 | — | — | — | 9.0 | — | 9.0 | — | — | 8.0 | — | 6.0 |
|  | .500 | 4.0 | 9.0 | — | 9.0 | 9.0 | 8.0 | 9.0 | 0.0 | 9.0 | 0.0 | 7.0 | 6.0 |
|  | .250 | 4.0 | 8.0 | — | 9.0 | 9.0 | 5.0 | 9.0 | 0.0 | 9.0 | 0.0 | 7.0 | 2.0 |
|  | .125 | 0.0 | 2.0 | — | 9.0 | 2.0 | 1.0 | 8.0 | 0.0 | 0.0 | 0.0 | 0.0 | 0.0 |
| 88 | 4.000 | 9.0 | — | — | 9.0 | 9.0 | 9.0 | — | — | 9.0 | — | 9.0 | — |
|  | 1.000 | 8.0 | 9.0 | — | 9.0 | 9.0 | 6.5 | 9.0 | 7.0 | 9.0 | 0.0 | 8.0 | 8.0 |
|  | .500 | 7.0 | 7.0 | — | 9.0 | 6.0 | 7.5 | 9.0 | 2.0 | 9.0 | 0.0 | 8.0 | 9.0 |
|  | .250 | 0.0 | 4.0 | — | 9.0 | 4.5 | 1.5 | 6.0 | 1.0 | 9.0 | 0.0 | 6.0 | 4.0 |
|  | .125 | 0.0 | 3.5 | — | 3.5 | 3.5 | 1.0 | 4.0 | 0.0 | 5.5 | 0.0 | 0.0 | 4.0 |
| 91 | 1.000 | 7.5 | 9.0 | 9.0 | 9.0 | 4.5 | 9.0 | 9.0 | 5.0 | 9.0 | 2.0 | — | 8.0 |
|  | .500 | 3.0 | 9.0 | 9.0 | 8.0 | 3.5 | 4.0 | 9.0 | 5.0 | 9.0 | 0.0 | — | 9.0 |
|  | .250 | 1.0 | 6.0 | 0.0 | 3.0 | 3.0 | 0.0 | 8.0 | 0.0 | 9.0 | 0.0 | — | 7.0 |
|  | .125 | 0.0 | 0.0 | 0.0 | 0.0 | 2.0 | 0.0 | 6.0 | 0.0 | 3.0 | 0.0 | — | 6.0 |
| 92 | 1.000 | 1.5 | 9.0 | — | 9.0 | 8.0 | 9.0 | 4.0 | 4.0 | 9.0 | 4.0 | — | 4.0 |
|  | .500 | 2.0 | 8.0 | — | 7.5 | 4.5 | 4.5 | 2.0 | 2.5 | 8.5 | 0.0 | 8.0 | 4.0 |
|  | .250 | 0.0 | 4.0 | — | 4.5 | 4.0 | 1.0 | 2.0 | 0.0 | 8.0 | 0.0 | 4.0 | 2.0 |
|  | .125 | 0.0 | 0.0 | — | 4.0 | 3.0 | 0.0 | 0.0 | 0.0 | 8.0 | 0.0 | 3.0 | 2.0 |
| 93 | 1.000 | 0.0 | — | — | — | 0.0 | — | 0.0 | — | — | 0.0 | — | 0.0 |
|  | .500 | 0.0 | — | — | — | 0.0 | — | 0.0 | — | — | 0.0 | — | 0.0 |
|  | .250 | 0.0 | — | — | — | 0.0 | — | 0.0 | — | — | 0.0 | — | 0.0 |
|  | .125 | 0.0 | — | — | — | 0.0 | — | 0.0 | — | — | 0.0 | — | 0.0 |
| 94 | 1.000 | 0.0 | 0.0 | — | 0.0 | 0.0 | 0.0 | 0.0 | 0.0 | 0.0 | 0.0 | 0.0 | 0.0 |
|  | .500 | 0.0 | 0.0 | — | 0.0 | 0.0 | 0.0 | 0.0 | 0.0 | 0.0 | 0.0 | 0.0 | 0.0 |
|  | .250 | 0.0 | 0.0 | — | 0.0 | 0.0 | 0.0 | 0.0 | 0.0 | 0.0 | 0.0 | 0.0 | 0.0 |
|  | .125 | 0.0 | 0.0 | — | 0.0 | 0.0 | 0.0 | 0.0 | 0.0 | 0.0 | 0.0 | 0.0 | 0.0 |
| 95 | 1.000 | 0.0 | 9.0 | — | 7.0 | 0.0 | 6.0 | 0.0 | 9.0 | 9.0 | 0.0 | 8.0 | 0.0 |
|  | .500 | 0.0 | 9.0 | — | 7.0 | 0.0 | 2.0 | 0.0 | 0.0 | 8.0 | 0.0 | 0.0 | 0.0 |
|  | .250 | 0.0 | 0.0 | — | 0.0 | 0.0 | 0.0 | 0.0 | 0.0 | 4.0 | 0.0 | 0.0 | 0.0 |
|  | .125 | 0.0 | 0.0 | — | 0.0 | 0.0 | 0.0 | 0.0 | 0.0 | 0.0 | 0.0 | 0.0 | 0.0 |
| 96 | 1.000 | 0.0 | — | — | — | 0.0 | — | 0.0 | — | — | 0.0 | — | 0.0 |
|  | .500 | 0.0 | — | — | — | 0.0 | — | 0.0 | — | — | 0.0 | — | 0.0 |
|  | .250 | 0.0 | — | — | — | 0.- | — | 0.0 | — | — | 0.0 | — | 0.0 |
|  | .125 | 0.0 | — | — | — | 0.0 | — | 0.0 | — | — | 0.0 | — | 0.0 |
| 97 | 1.000 | 9.0 | — | — | — | 4.0 | — | 9.0 | — | — | 7.0 | — | 4.0 |
|  | .500 | 9.0 | — | — | — | 2.0 | — | 9.0 | — | — | 3.0 | — | 2.0 |
|  | .250 | 9.0 | — | — | — | 0.0 | — | 9.0 | — | — | 0.0 | — | 0.0 |
|  | .125 | 4.0 | — | — | — | 0.0 | — | 9.0 | — | — | 0.0 | — | 0.0 |
| 98 | 1.000 | 9.0 | — | — | — | 9.0 | — | 9.0 | — | — | 6.0 | — | 2.0 |
|  | .500 | 9.0 | — | — | — | 4.0 | — | 9.0 | — | — | 1.0 | — | 0.0 |
|  | .250 | 9.0 | — | — | — | 2.0 | — | 8.0 | — | — | 0.0 | — | 0.0 |
|  | .125 | 8.3 | — | — | — | 2.0 | — | 4.0 | — | — | 0.0 | — | 0.0 |
| 99 | 1.000 | 9.0 | — | 9.0 | 9.0 | 1.3 | 9.0 | 9.0 | — | 9.0 | 7.3 | 9.0 | 1.3 |
|  | .500 | 8.0 | — | 9.0 | 9.0 | 0.0 | 9.0 | 9.0 | — | 9.0 | 5.0 | 6.0 | 0.0 |
|  | .250 | 5.5 | — | 9.0 | 9.0 | 0.0 | 7.0 | 9.0 | — | 9.0 | 2.7 | 5.0 | 0.0 |
|  | .125 | 3.3 | — | 6.0 | 7.0 | 0.0 | 7.0 | 8.5 | — | 7.0 | 0.7 | 0.0 | 0.0 |
| 100 | 1.000 | 0.0 | — | — | — | 0.0 | — | 0.0 | — | — | 0.0 | — | 0.0 |
|  | .500 | 0.0 | — | — | — | 0.0 | — | 0.0 | — | — | 0.0 | — | 0.0 |
|  | .250 | 0.0 | — | — | — | 0.0 | — | 0.0 | — | — | 0.0 | — | 0.0 |
|  | .125 | 0.0 | — | — | — | 0.0 | — | 0.0 | — | — | 0.0 | — | 0.0 |
| 101 | 1.000 | 9.0 | — | — | — | 9.0 | — | 9.0 | — | — | 9.0 | — | 7.0 |
|  | .500 | 9.0 | — | — | — | 6.0 | — | 9.0 | — | — | 8.0 | — | 7.0 |
|  | .250 | 9.0 | — | — | — | 6.0 | — | 9.0 | — | — | 7.0 | — | 6.0 |
|  | .125 | 6.0 | — | — | — | 4.0 | — | 9.0 | — | — | 6.0 | — | 2.0 |
| 102 | 4.000 | 9.0 | — | — | 9.0 | 9.0 | 9.0 | — | — | 9.0 | — | 9.0 | |
|  | 1.000 | 7.0 | — | — | — | 9.0 | — | 9.0 | — | — | 9.0 | — | 8.0 |
|  | .250 | 9.0 | — | — | — | 9.0 | — | 9.0 | — | — | 9.0 | — | 7.0 |
|  | .125 | 4.0 | — | — | — | 2.0 | — | 9.0 | — | — | 6.0 | — | 7.0 |
| 103 | 1.000 | 8.0 | 9.0 | — | 9.0 | 4.0 | 9.0 | 9.0 | 0.0 | 9.0 | 7.0 | 8.0 | 4.0 |
|  | .500 | 6.0 | 9.0 | — | 8.0 | 0.0 | 9.0 | 9.0 | 0.0 | 9.0 | 4.0 | 5.0 | 0.0 |
|  | .250 | 4.0 | 6.0 | — | 9.0 | 0.0 | 5.0 | 9.0 | 0.0 | 9.0 | 4.0 | 0.0 | 0.0 |
|  | .125 | 2.0 | 2.0 | — | 6.0 | 0.0 | 0.0 | 8.0 | 0.0 | 8.0 | 4.0 | 0.0 | 0.0 |
| 104 | 4.000 | 9.0 | — | — | 9.0 | 0.0 | 9.0 | — | — | 9.0 | — | 6.0 | — |
|  | 1.000 | 9.0 | — | — | — | 7.0 | — | 9.0 | — | — | 9.0 | — | 8.0 |
|  | .500 | 9.0 | — | — | — | 0.0 | — | 9.0 | — | — | 6.0 | — | 7.0 |
|  | .250 | 7.0 | — | — | — | 0.0 | — | 9.0 | — | — | 0.0 | — | 0.0 |
|  | .125 | 6.0 | — | — | — | 0.0 | — | 9.0 | — | — | 0.0 | — | 0.0 |
| 105 | 4.000 | 9.0 | — | — | 9.0 | 9.0 | 9.0 | — | — | 9.0 | — | 5.0 | — |
|  | 1.000 | 9.0 | — | — | — | 9.0 | — | 9.0 | — | — | 9.0 | — | 9.0 |
|  | .500 | 8.0 | — | — | — | 7.0 | — | 9.0 | — | — | 7.0 | — | 7.0 |
|  | .250 | 2.0 | — | — | — | 2.0 | — | 9.0 | — | — | 7.0 | — | 4.0 |
|  | .125 | 0.0 | — | — | — | 4.0 | — | 7.0 | — | — | 4.0 | — | 4.0 |
| 106 | 4.000 | 9.0 | — | — | 9.0 | 7.0 | 9.0 | — | — | 9.0 | — | 8.0 | — |
|  | 1.000 | 9.0 | — | — | — | 9.0 | — | 9.0 | — | — | 9.0 | — | 9.0 |
|  | .500 | 9.0 | — | — | — | 2.0 | — | 9.0 | — | — | 8.0 | — | 9.0 |
|  | .250 | 8.0 | — | — | — | 2.0 | — | 9.0 | — | — | 7.0 | — | 8.0 |

TABLE XI-continued

PRE-EMERGENCE TESTS - RATES IN KG/HA

| Compound of EXAMPLE | Rate | BA | BG | CH | FO | PN | WO | ST | MA | WM | SE | VL | BR |
|---|---|---|---|---|---|---|---|---|---|---|---|---|---|
| | .125 | 4.0 | — | — | — | 0.0 | — | 8.0 | — | — | — | — | 4.0 |
| 107 | 1.000 | 0.0 | — | — | — | 0.0 | — | 0.0 | — | — | — | — | 2.0 |
| | .500 | 0.0 | — | — | — | 0.0 | — | 0.0 | — | — | 0.0 | — | 1.0 |
| | .250 | 0.0 | — | — | — | 0.0 | — | 0.0 | — | — | 0.0 | — | 0.0 |
| | .125 | 0.0 | — | — | — | 0.0 | — | 0.0 | — | — | 0.0 | — | 0.0 |
| 108 | 1.000 | 0.0 | — | — | — | 0.0 | — | 0.0 | — | — | 0.0 | — | 0.0 |
| | .500 | 0.0 | — | — | — | 0.0 | — | 0.0 | — | — | 0.0 | — | 0.0 |
| | .250 | 0.0 | — | — | — | 0.0 | — | 0.0 | — | — | 0.0 | — | 0.0 |
| | .125 | 0.0 | — | — | — | 0.0 | — | 0.0 | — | — | 0.0 | — | 0.0 |
| 109 | 1.000 | 0.0 | — | — | — | 0.0 | — | 0.0 | — | — | 0.0 | — | 0.0 |
| | .500 | 0.0 | — | — | — | 0.0 | — | 0.0 | — | — | 0.0 | — | 0.0 |
| | .250 | 0.0 | — | — | — | 0.0 | — | 0.0 | — | — | 0.0 | — | 0.0 |
| | .125 | 0.0 | — | — | — | 0.0 | — | 0.0 | — | — | 0.0 | — | 0.0 |
| 110 | 4.000 | 9.0 | — | — | 9.0 | 0.0 | 8.0 | — | — | 9.0 | — | 8.0 | — |
| | 1.000 | 2.0 | — | — | — | 2.0 | — | 9.0 | — | — | 4.0 | — | 4.0 |
| | .500 | 0.0 | — | — | — | 1.0 | — | 9.0 | — | — | 1.0 | — | 2.0 |
| | .250 | 0.0 | — | — | — | 0.0 | — | 4.0 | — | — | 0.0 | — | 1.0 |
| | .125 | 0.0 | — | — | — | 0.0 | — | 2.0 | — | — | 0.0 | — | 0.0 |
| 111 | 1.000 | 9.0 | — | — | — | 6.0 | — | 9.0 | — | — | 2.0 | — | 4.0 |
| | .500 | 7.0 | — | — | — | 5.0 | — | 9.0 | — | — | 2.0 | — | 4.0 |
| | .250 | 2.0 | — | — | — | 2.0 | — | 9.0 | — | — | 0.0 | — | — |
| | .125 | 4.0 | — | — | — | 0.0 | — | 9.0 | — | — | 0.0 | — | 0.0 |
| 114 | 1.000 | 9.0 | — | 7.0 | 9.0 | 8.5 | 9.0 | 9.0 | — | 9.0 | 7.3 | 8.0 | 7.0 |
| | .500 | 7.6 | — | 7.0 | 9.0 | 6.7 | 8.0 | 8.6 | — | 9.0 | 4.8 | 8.0 | 6.5 |
| | .250 | 5.4 | — | 6.0 | 9.0 | 5.4 | 5.0 | 5.7 | — | 9.0 | 2.0 | 7.0 | 4.7 |
| | .125 | 3.0 | — | 6.0 | 7.0 | 3.0 | 2.0 | 5.5 | — | 8.0 | 0.4 | 3.0 | 2.2 |
| 115 | 4.000 | 9.0 | — | — | 9.0 | 6.0 | 9.0 | — | — | 9.0 | — | 9.0 | — |
| | 1.000 | 4.0 | — | — | — | 7.0 | — | 8.0 | — | — | 6.0 | — | 9.0 |
| | .500 | 4.0 | — | — | — | 6.0 | — | 9.0 | — | — | 0.0 | — | 7.0 |
| | .250 | 0.0 | — | — | — | 6.0 | — | 7.0 | — | — | 0.0 | — | 6.0 |
| | .125 | 0.0 | — | — | — | 0.0 | — | 7.0 | — | — | 0.0 | — | 0.0 |
| 116 | 1.000 | 9.0 | — | — | — | 6.0 | — | 9.0 | — | — | 9.0 | — | 6.0 |
| | .500 | 8.0 | — | — | — | 4.0 | — | 9.0 | — | — | 7.0 | — | 6.0 |
| | .250 | 6.0 | — | — | — | 2.0 | — | 9.0 | — | — | 2.0 | — | 4.0 |
| | .125 | 6.0 | — | — | — | 0.0 | — | 7.0 | — | — | 0.0 | — | 0.0 |
| 117 | 1.000 | 4.0 | — | — | — | 2.0 | — | 7.0 | — | — | 8.0 | — | 2.0 |
| | .500 | 1.0 | — | — | — | 2.0 | — | 2.0 | — | — | 6.0 | — | 2.0 |
| | .250 | 0.0 | — | — | — | 0.0 | — | 0.0 | — | — | 4.0 | — | 0.0 |
| | .125 | 0.0 | — | — | — | 0.0 | — | 0.0 | — | — | 0.0 | — | 0.0 |
| 118 | 1.000 | 9.0 | — | — | — | 4.0 | — | 9.0 | — | — | 2.0 | — | 6.0 |
| | .500 | 9.0 | — | — | — | 0.0 | — | 9.0 | — | — | 0.0 | — | 2.0 |
| | .250 | 9.0 | — | — | — | 0.0 | — | 9.0 | — | — | 0.0 | — | 0.0 |
| | .125 | 4.0 | — | — | — | 0.0 | — | 6.0 | — | — | 0.0 | — | 0.0 |
| 119 | 1.000 | 2.0 | — | — | — | 2.0 | — | 8.0 | — | — | 4.0 | — | 2.0 |
| | .500 | 0.0 | — | — | — | 0.0 | — | 6.0 | — | — | 0.0 | — | 0.0 |
| | .250 | 0.0 | — | — | — | 0.0 | — | 2.0 | — | — | 0.0 | — | 0.0 |
| | .125 | 0.0 | — | — | — | 0.0 | — | 0.0 | — | — | 0.0 | — | 0.0 |
| 120 | 1.000 | 7.0 | — | — | — | 2.0 | — | 9.0 | — | — | 2.0 | — | 4.0 |
| | .500 | 7.0 | — | — | — | 2.0 | — | 4.0 | — | — | 2.0 | — | 2.0 |
| | .250 | 0.0 | — | — | — | 0.0 | — | 0.0 | — | — | 0.0 | — | 0.0 |
| | .125 | 0.0 | — | — | — | 0.0 | — | 0.0 | — | — | 0.0 | — | 0.0 |
| 121 | 1.000 | 4.0 | — | — | — | 6.0 | — | 9.0 | — | — | 8.0 | — | 6.0 |
| | .500 | 4.0 | — | — | — | 6.0 | — | 9.0 | — | — | 8.0 | — | — |
| | .250 | 2.0 | — | — | — | 2.0 | — | 0.0 | — | — | 0.0 | — | 2.0 |
| | .125 | 0.0 | — | — | — | 0.0 | — | 0.0 | — | — | 0.0 | — | 0.0 |
| 122 | 1.000 | 4.0 | — | — | — | 2.0 | — | 9.0 | — | — | 6.0 | — | 2.0 |
| | .500 | 2.0 | — | — | — | — | — | 6.0 | — | — | 0.0 | — | 0.0 |
| | .250 | 0.0 | — | — | — | 0.0 | — | 0.0 | — | — | 0.0 | — | 0.0 |
| | .125 | 0.0 | — | — | — | 0.0 | — | 0.0 | — | — | 0.0 | — | 0.0 |
| 123 | 1.000 | 9.0 | — | — | — | 9.0 | — | 9.0 | — | — | 9.0 | — | 9.0 |
| | .500 | 9.0 | — | — | — | 9.0 | — | 9.0 | — | — | 9.0 | — | 9.0 |
| | .250 | 9.0 | — | — | — | 4.0 | — | 9.0 | — | — | 9.0 | — | 4.0 |
| | .125 | 9.0 | — | — | — | 2.0 | — | 9.0 | — | — | 3.0 | — | 4.0 |
| 124 | 1.000 | 2.0 | — | — | — | 2.0 | — | 2.0 | — | — | 3.0 | — | 2.0 |
| | .500 | 0.0 | — | — | — | 0.0 | — | 0.0 | — | — | 0.0 | — | 0.0 |
| | .250 | 0.0 | — | — | — | 0.0 | — | 0.0 | — | — | 0.0 | — | 0.0 |
| | .125 | 0.0 | — | — | — | 0.0 | — | 0.0 | — | — | 0.0 | — | 0.0 |
| 125 | 1.000 | 9.0 | — | — | — | 9.0 | — | 9.0 | — | — | 9.0 | — | 6.0 |
| | .500 | 4.0 | — | — | — | 4.0 | — | 4.0 | — | — | 8.0 | — | 4.0 |
| | .250 | 2.0 | — | — | — | 0.0 | — | 2.0 | — | — | 4.0 | — | 2.0 |
| | .125 | 0.0 | — | — | — | 0.0 | — | 0.0 | — | — | 0.0 | — | 0.0 |
| 126 | 1.000 | 4.0 | — | — | — | 4.0 | — | 8.0 | — | — | 8.0 | — | 4.0 |
| | .500 | 4.0 | — | — | — | 4.0 | — | 8.0 | — | — | 4.0 | — | 4.0 |
| | .250 | 0.0 | — | — | — | 0.0 | — | 2.0 | — | — | 0.0 | — | 0.0 |
| | .125 | 0.0 | — | — | — | 0.0 | — | 0.0 | — | — | 0.0 | — | 0.0 |
| 127 | 4.000 | 9.0 | — | — | 9.0 | 9.0 | 9.0 | — | — | 8.0 | — | 9.0 | — |
| | 1.000 | 9.0 | — | — | — | 6.0 | — | 9.0 | — | — | 2.0 | — | 6.0 |
| | .500 | 8.0 | — | — | — | 4.0 | — | 8.0 | — | — | 2.0 | — | 5.0 |
| | .250 | 0.0 | — | — | — | 0.0 | — | 1.0 | — | — | 0.0 | — | 2.0 |

TABLE XI-continued

PRE-EMERGENCE TESTS - RATES IN KG/HA

| Compound of EXAMPLE | Rate | BA | BG | CH | FO | PN | WO | ST | MA | WM | SE | VL | BR |
|---|---|---|---|---|---|---|---|---|---|---|---|---|---|
| | .125 | 0.0 | — | — | — | 0.0 | — | 0.0 | — | — | 0.0 | — | 0.0 |
| 128 | 4.000 | 7.0 | — | — | 8.0 | 0.0 | 0.0 | — | — | 8.0 | — | 8.0 | — |
| 130 | 4.000 | 9.0 | — | — | 9.0 | 4.0 | 9.0 | — | — | 8.0 | — | 9.0 | — |
| 131 | 4.000 | 8.0 | — | — | 8.0 | 0.0 | 5.0 | — | — | 8.0 | — | 7.0 | — |
| 137 | 1.000 | 6.5 | 9.0 | 9.0 | 4.0 | 9.0 | 7.0 | 9.0 | 4.0 | 9.0 | 6.0 | — | 9.0 |
| | .500 | 3.0 | 3.0 | 9.0 | 5.0 | 4.5 | 5.0 | 4.0 | 0.0 | 8.0 | 1.0 | — | 8.0 |
| | .250 | 1.0 | 0.0 | 4.0 | 0.0 | 2.0 | 0.0 | 4.0 | 0.0 | 8.0 | 0.0 | — | 8.0 |
| | .125 | 0.0 | 0.0 | 0.0 | 0.0 | 2.0 | 0.0 | 0.0 | 2.0 | 0.0 | 0.0 | — | 6.0 |
| 138 | 1.000 | 2.0 | 4.0 | 9.0 | 6.0 | 6.0 | 4.0 | 6.0 | 0.0 | 9.0 | 2.0 | — | 4.0 |
| | .500 | 0.0 | 0.0 | 9.0 | 0.0 | 2.0 | 2.0 | 1.0 | 0.0 | 8.0 | 1.0 | — | 4.0 |
| | .250 | 0.0 | 0.0 | 9.0 | 0.0 | 1.0 | 0.0 | 0.0 | 0.0 | 8.0 | 0.0 | — | 2.0 |
| | .125 | 0.0 | 0.0 | 5.0 | 0.0 | 1.0 | 0.0 | 0.0 | 0.0 | 6.0 | 0.0 | — | 0.0 |
| 139 | 1.000 | 3.0 | 6.0 | 9.0 | 9.0 | 6.5 | 0.0 | 0.0 | 0.0 | 8.0 | 0.0 | — | 6.0 |
| | .500 | 0.0 | 0.0 | 0.0 | 0.0 | 0.5 | 0.0 | 0.0 | 0.0 | 8.0 | 0.0 | — | 4.0 |
| | .250 | 0.0 | 0.0 | 0.0 | 0.0 | 0.0 | 0.0 | 0.0 | 0.0 | 4.0 | 0.0 | — | 4.0 |
| | .125 | 0.0 | 0.0 | 0.0 | 0.0 | 0.0 | 0.0 | 0.0 | 0.0 | 3.0 | 0.0 | — | 2.0 |
| 140 | 1.000 | 9.0 | — | — | — | 9.0 | — | 9.0 | — | — | 9.0 | — | 4.0 |
| | .500 | 9.0 | — | — | — | 6.0 | — | 9.0 | — | — | 4.0 | — | 4.0 |
| | .250 | 0.0 | — | — | — | 0.0 | — | 0.0 | — | — | 2.0 | — | 0.0 |
| | .125 | 0.0 | — | — | — | 0.0 | — | 0.0 | — | — | 0.0 | — | 0.0 |
| 141 | 1.000 | 0.0 | — | — | — | 0.0 | — | 0.0 | — | — | 0.0 | — | 0.0 |
| | .500 | 0.0 | — | — | — | 0.0 | — | 0.0 | — | — | 0.0 | — | 0.0 |
| | .250 | 0.0 | — | — | — | 0.0 | — | 0.0 | — | — | 0.0 | — | 0.0 |
| | .125 | 0.0 | — | — | — | 0.0 | — | 0.0 | — | — | 0.0 | — | 0.0 |

EXAMPLE 143

Rice Tolerance to Post-Transplanting Applications

The selectivity of the compounds included among Examples 72–141 is exemplified using the procedure of Example 69 on two ten-day old rice seedlings (cv. S-201 or cv. Newbonnett).

The data are reported in Table XII.

TABLE XII

Rice tolerance to post-transplanting applications

| Compound of Example | 1.0 | 0.5 | 0.25 | 0.125 |
|---|---|---|---|---|
| 72 | 0.0 | 0.0 | 0.0 | 0.0 |
| 76 | 0.0 | 0.0 | 0.0 | 0.0 |
| 77 | 2.0 | 1.0 | 0.0 | 0.0 |
| 78 | 4.0 | 2.0 | 0.7 | 0.7 |
| 79 | 5.5 | 4.0 | 1.0 | 0.0 |
| 80 | 8.0 | 8.0 | 7.0 | 6.0 |
| 81 | 0.0 | 0.0 | 0.0 | 0.0 |
| 82 | 0.0 | 0.0 | 0.0 | 0.0 |
| 83 | 0.0 | 0.0 | 0.0 | 0.0 |
| 84 | 5.5 | 5.0 | 4.5 | 4.5 |
| 85 | 0.0 | 0.0 | 0.0 | 0.0 |
| 86 | 7.0 | 4.0 | 3.0 | 1.0 |
| 87 | 8.0 | 8.0 | 7.0 | 4.0 |
| 88 | 1.0 | 1.0 | 0.0 | 0.0 |
| 91 | 7.0 | 3.0 | 2.0 | 2.0 |
| 92 | 3.0 | 4.0 | 3.0 | 2.0 |
| 93 | 1.0 | 1.0 | 1.0 | 0.0 |
| 94 | 1.0 | 0.0 | 0.0 | 0.0 |
| 95 | 0.0 | 0.0 | 0.0 | 0.0 |
| 96 | 0.0 | 0.0 | 0.0 | 0.0 |
| 97 | 8.0 | 7.0 | 6.0 | 3.0 |
| 98 | 7.0 | 6.0 | 2.0 | 2.0 |
| 99 | 7.0 | 4.0 | 2.0 | 1.0 |
| 100 | 0.0 | 0.0 | 0.0 | 0.0 |
| 101 | 7.0 | 7.0 | 6.0 | 2.0 |
| 102 | 7.0 | 7.0 | 6.0 | 6.0 |
| 103 | 6.0 | 3.0 | 3.0 | 0.0 |
| 104 | 8.0 | 8.0 | 4.0 | 0.0 |
| 105 | 7.0 | 2.0 | 2.0 | 0.0 |
| 106 | 7.0 | 7.0 | 4.0 | 0.0 |
| 107 | 0.0 | 0.0 | 0.0 | 0.0 |
| 108 | 0.0 | 0.0 | 0.0 | 0.0 |
| 109 | 0.0 | 0.0 | 0.0 | 0.0 |
| 110 | 0.0 | 0.0 | 0.0 | 0.0 |
| 111 | 4.0 | 2.0 | 0.0 | 0.0 |
| 114 | 2.5 | 1.5 | 0.5 | 0.0 |
| 115 | 0.0 | 0.0 | 0.0 | 0.0 |
| 118 | 3.0 | 3.0 | 1.0 | 0.0 |
| 119 | 1.0 | 0.0 | 0.0 | 0.0 |
| 120 | 2.0 | 0.0 | 0.0 | 0.0 |
| 121 | 2.0 | 0.0 | 0.0 | 0.0 |
| 122 | 1.0 | 0.0 | 0.0 | 0.0 |
| 123 | 2.0 | 1.0 | 0.0 | 0.0 |
| 124 | 0.0 | 0.0 | 0.0 | 0.0 |
| 125 | 1.0 | 0.0 | 0.0 | 0.0 |
| 126 | 0.0 | 0.0 | 0.0 | 0.0 |
| 127 | 1.0 | 0.0 | 0.0 | 0.0 |
| 137 | 2.0 | 1.0 | 0.0 | 0.0 |
| 138 | 0.0 | 0.0 | 0.0 | 0.0 |
| 139 | 0.0 | 0.0 | 0.0 | 0.0 |
| 140 | 2.0 | 0.0 | 0.0 | 0.0 |
| 141 | 0.0 | 0.0 | 0.0 | 0.0 |

EXAMPLE 144

Postemergence Herbicial Activity and Selectivity in Transplanted and Direct-Seeded Rice The postemergence herbicidal activity and rice selectivity of some of the compounds of Examples 72–141 are exemplified using the procedure of Example 70. The data are reported in Table XIII below.

TABLE XIII

Postemergence herbicidal activity and selectivity in rice of compounds having the structure

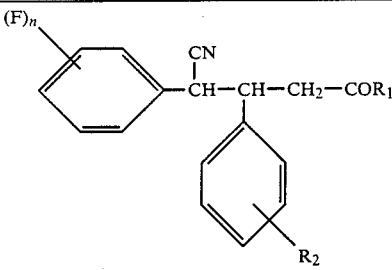

| ERYTHRO-/THREO* | Compound R₁ | R₂ | (F)ₙ | RATE | BA | PN | RR | ST | SE | BR | Rice RL | RK | RN |
|---|---|---|---|---|---|---|---|---|---|---|---|---|---|
| 57/43 | OCH₃ | 3-Br | 3,4-diF | 1.000 | 6.5 | 0.0 | 7.0 | 9.0 | 7.0 | 0.0 | 2.0 | 0.0 | 0.0 |
|  |  |  |  | .500 | 4.5 | 0.0 | 4.0 | 9.0 | 2.0 | 0.0 | 1.0 | 0.0 | 0.0 |
|  |  |  |  | .250 | 4.0 | 0.0 | 0.0 | 9.0 | 0.0 | 0.0 | 0.0 | 0.0 | 0.0 |
|  |  |  |  | .125 | 1.0 | 0.0 | 0.0 | 2.0 | 0.0 | 0.0 | 0.0 | 0.0 | 0.0 |
| 60/40 | OCH₃ | 4-Br | 4-F | 1.000 | 4.0 | 1.7 | 2.0 | 9.0 | 0.0 | 1.0 | 0.0 | 0.0 | 0.0 |
|  |  |  |  | .500 | 1.0 | 0.0 | 0.5 | 8.0 | 0.0 | 0.0 | 0.0 | 0.0 | 0.0 |
|  |  |  |  | .250 | 0.0 | 0.0 | 0.0 | 3.0 | 0.0 | 0.0 | 0.0 | 0.0 | 0.0 |
|  |  |  |  | .125 | 0.0 | 0.0 | 0.0 | 1.0 | 0.0 | 0.0 | 0.0 | 0.0 | 0.0 |
| 58/42 | OCH₃ | 3-CF₃ | 3,4-diF | 1.000 | 0.0 | 0.0 | 4.0 | 9.0 | 4.0 | 4.0 | — | 1.0 | — |
|  |  |  |  | .500 | 0.0 | 0.0 | 2.0 | 4.0 | 0.0 | 2.0 | — | 0.0 | — |
|  |  |  |  | .250 | 0.0 | 0.0 | 0.0 | 2.0 | 0.0 | 1.0 | — | 0.0 | — |
|  |  |  |  | .125 | 0.0 | 0.0 | 0.0 | 2.0 | 0.0 | 0.0 | — | 0.0 | — |
| 55/45 | OCH₃ | 2,4-diF | 3,4-diF | 1.000 | 8.0 | 9.0 | 9.0 | 9.0 | 0.0 | 8.0 | — | 0.0 | — |
|  |  |  |  | .500 | 2.0 | 9.0 | 9.0 | 9.0 | 0.0 | 6.0 | — | 0.0 | — |
|  |  |  |  | .250 | 0.0 | 2.0 | 8.0 | 4.0 | 0.0 | 4.0 | — | 0.0 | — |
|  |  |  |  | .125 | 0.0 | 0.0 | 7.0 | 2.0 | 0.0 | 2.0 | — | 0.0 | — |
| 55/45 | OCH₃ | 3,5-diF | 4-F | 1.000 | 8.0 | 8.0 | 8.0 | 9.0 | 0.0 | 2.0 | — | 2.0 | — |
|  |  |  |  | .500 | 4.0 | 2.0 | 7.0 | 9.0 | 0.0 | 2.0 | — | 1.0 | — |
|  |  |  |  | .250 | 1.0 | 2.5 | 4.0 | 8.0 | 0.0 | 2.0 | — | 2.0 | — |
|  |  |  |  | .125 | 0.0 | 0.0 | 0.0 | 0.0 | 0.0 | 2.0 | — | 0.0 | — |
| 60/40 | OCH₃ | 3-Cl | 3,5-diF | .500 | 9.0 | 0.0 | 0.0 | 7.0 | 6.0 | 2.0 | — | 7.0 | — |
|  |  |  |  | .250 | 9.0 | 0.0 | 7.0 | 9.0 | 6.0 | 4.0 | — | 3.0 | — |
|  |  |  |  | .125 | 8.0 | 0.0 | 4.0 | 8.0 | 0.0 | 0.0 | — | 3.0 | — |
| 60/40 | OCH₃ | 3-F | 3-Cl—4-F | 1.000 | 9.0 | 4.0 | 8.0 | 9.0 | 0.0 | 7.0 | — | 3.0 | — |
|  |  |  |  | .500 | 9.0 | 1.0 | 8.0 | 9.0 | 0.0 | 4.0 | — | — | — |
|  |  |  |  | .250 | 9.0 | 1.0 | 2.0 | 9.0 | 0.0 | 2.0 | — | — | — |
|  |  |  |  | .125 | 4.0 | 0.0 | 0.0 | 8.0 | 0.0 | 0.0 | — | 2.0 | — |
| 67/33 | OCH₃ | 2,6-diF | 3-F | 1.000 | 9.0 | 2.0 | 9.0 | 9.0 | 2.0 | 7.0 | — | 8.0 | — |
|  |  |  |  | .500 | 8.0 | 2.0 | 9.0 | 9.0 | 1.0 | 4.0 | — | 7.0 | — |
|  |  |  |  | .250 | 7.0 | 1.0 | 8.0 | 8.0 | 0.0 | 2.0 | — | 3.0 | — |
|  |  |  |  | .125 | 2.0 | 0.0 | 7.0 | 4.0 | 0.0 | 0.0 | — | 2.0 | — |
| 53/47 | OCH₃ | 2,5-diF | 3-F | 1.000 | 9.0 | 7.0 | 8.0 | 9.0 | 4.0 | 7.0 | — | 9.0 | — |
|  |  |  |  | .500 | 9.0 | 7.0 | 8.0 | 9.0 | 4.0 | 7.0 | — | 8.0 | — |
|  |  |  |  | .250 | 8.0 | 2.0 | 8.0 | 8.0 | 2.0 | 4.0 | — | 7.0 | — |
|  |  |  |  | .125 | 8.0 | 0.0 | 8.0 | 8.0 | 0.0 | 0.0 | — | 3.0 | — |
| 57/43 | OCH₃ | 3-OCH—F₂ | 3,4-diF | 1.000 | 0.0 | 0.0 | 0.0 | 9.0 | 0.0 | 0.0 | — | 0.0 | — |
|  |  |  |  | .500 | 0.0 | 0.0 | 0.0 | 7.0 | 0.0 | 0.0 | — | 0.0 | — |
|  |  |  |  | .250 | 0.0 | 0.0 | 0.0 | 7.0 | 0.0 | 0.0 | — | 0.0 | — |
|  |  |  |  | .125 | 0.0 | 0.0 | 0.0 | 4.0 | 0.0 | 0.0 | — | 0.0 | — |
| 53/46 | OCH₃ | 2-F—5-Br | 3,4-diF | 1.000 | 8.0 | 0.0 | 7.0 | 9.0 | 9.0 | 8.0 | — | — | — |
|  |  |  |  | .500 | 2.0 | 0.0 | 7.0 | 9.0 | 8.0 | 6.0 | — | 0.0 | — |
|  |  |  |  | .250 | 0.0 | 0.0 | 4.0 | 9.0 | 8.0 | 0.0 | — | 0.0 | — |
|  |  |  |  | .125 | 0.0 | 0.0 | 4.0 | 8.0 | 4.0 | 0.0 | — | 0.0 | — |
| 51/49 | OCH₃ | 2-F—5-Cl | 4-F | 1.000 | 4.0 | 4.0 | 2.0 | 9.0 | 8.0 | 8.0 | — | 2.0 | — |
|  |  |  |  | .500 | 0.0 | 0.0 | 2.0 | 8.0 | 6.0 | 2.0 | — | 1.0 | — |
|  |  |  |  | .250 | 0.0 | 0.0 | 0.0 | 8.0 | 0.0 | 0.0 | — | 0.0 | — |
|  |  |  |  | .125 | 0.0 | 0.0 | 0.0 | 7.0 | 0.0 | 0.0 | — | 0.0 | — |
| 53/47 | OCH₃ | 2-F—5-Cl | 3,4-diF | 1.000 | 9.0 | 6.0 | 9.0 | 9.0 | 8.0 | 8.0 | — | 7.0 | — |
|  |  |  |  | .500 | 9.0 | 0.0 | 8.0 | 9.0 | 8.0 | 4.0 | — | 3.0 | — |
|  |  |  |  | .250 | 9.0 | 0.0 | 8.0 | 9.0 | 4.0 | 4.0 | — | 2.0 | — |
|  |  |  |  | .125 | 8.0 | 0.0 | 2.0 | 8.0 | 2.0 | 8.0 | — | 1.0 | — |
| 56/44 | OCH₃ | 4-OCH₃ | 3-F | 1.000 | 4.3 | 4.6 | 0.7 | 1.2 | 0.0 | 5.8 | — | 0.0 | — |
|  |  |  |  | .500 | 3.1 | 3.0 | 0.9 | 0.8 | 0.0 | 3.9 | — | 0.0 | — |
|  |  |  |  | .250 | 1.6 | 2.4 | 0.2 | 0.0 | 0.0 | 1.8 | — | 0.0 | — |
|  |  |  |  | .125 | 1.1 | 1.8 | 0.0 | 0.0 | 0.0 | 1.9 | — | 0.0 | — |
| 57/43 | OCH₃ | 3-OCH₃ | 3-F | 1.000 | 9.0 | 7.0 | — | — | — | — | — | — | — |
|  |  |  |  | .500 | 7.0 | 2.0 | 0.0 | 0.0 | 0.0 | 0.0 | — | 0.0 | — |
|  |  |  |  | .250 | 4.0 | 1.0 | 0.0 | 0.0 | 0.0 | 0.0 | — | 0.0 | — |
|  |  |  |  | .125 | 2.5 | 0.0 | 0.0 | 0.0 | 0.0 | 0.0 | — | 0.0 | — |
| 5/95 | OCH₃ | 4-OCH₃ | 3-F | 1.000 | 8.0 | 9.0 | 7.0 | 7.0 | 3.0 | 9.0 | — | 2.0ᵃ | — |
|  |  |  |  | .500 | 6.0 | 8.0 | 6.0 | 2.0 | 1.0 | 8.0 | — | 1.0 | — |
|  |  |  |  | .250 | 4.0 | 6.0 | 4.0 | 0.0 | 0.0 | 8.0 | — | 1.0 | — |

TABLE XIII-continued

Postemergence herbicidal activity and selectivity in rice of compounds having the structure

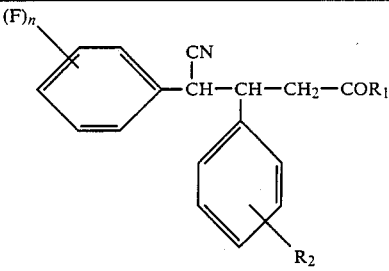

| ERYTHRO/-THREO* | Compound R₁ | R₂ | (F)ₙ | RATE | BA | PN | RR | ST | SE | BR | Rice RL | RK | RN |
|---|---|---|---|---|---|---|---|---|---|---|---|---|---|
| | | | | .125 | 1.0 | — | 2.0 | 0.0 | 0.0 | 2.0 | — | 0.0 | — |
| 61/39 | OC₂H₅ | 4-OCH₃ | 3-F | 1.000 | 8.0 | 7.0 | 2.0 | 1.0 | 0.0 | 8.0 | — | 1.0ᵃ | — |
| | | | | .500 | 2.0 | 2.0 | 1.0 | 0.0 | 0.0 | 2.0 | — | 0.0 | — |
| | | | | .250 | 2.0 | 0.0 | 0.0 | 0.0 | 0.0 | 0.0 | — | 0.0 | — |
| | | | | .125 | 0.0 | 0.0 | 0.0 | 0.0 | 0.0 | 2.0 | — | 0.0 | — |
| 62/38 | OC₃H₇—n | 4-OCH₃ | 3-F | 1.000 | 6.0 | 0.0 | 2.0 | 0.0 | 0.0 | 7.0 | — | 2.0ᵃ | — |
| | | | | .500 | 2.0 | 0.0 | 1.0 | 0.0 | 0.0 | 7.0 | — | 2.0 | — |
| | | | | .250 | 2.0 | 0.0 | 0.0 | 0.0 | 0.0 | 4.0 | — | 1.0 | — |
| | | | | .125 | 0.0 | 0.0 | 0.0 | 0.0 | 0.0 | 2.0 | — | 0.0 | — |
| 58/42 | OC₃H₇—i | 4-OCH₃ | 3-F | 1.000 | 6.0 | 4.0 | 4.0 | 0.0 | 0.0 | 2.0 | — | 2.0ᵃ | — |
| | | | | .500 | 4.0 | 1.0 | 2.0 | 0.0 | 0.0 | 1.0 | — | 1.0 | — |
| | | | | .250 | 0.0 | 0.0 | 0.0 | 0.0 | 0.0 | 0.0 | — | 0.0 | — |
| | | | | .125 | 0.0 | 0.0 | 0.0 | 0.0 | 0.0 | 0.0 | — | 0.0 | — |

ᵃCv. Newbonnet

EXAMPLE 145

Preemergence Herbicidal Activity and Selectivity in Wheat and Barley

The preemergence herbicidal activity and selectivity of some of the compounds included among Examples 72–141 is exemplified using the procedure of Example 71. The data are listed in Table XIV below.

TABLE XIV

Preemergence herbicidal activity and selectivity in wheat and barley of compounds having the structure $$\underset{(F)_n}{\text{C}_6\text{H}_4}-\underset{\underset{\text{CN}}{|}}{\text{CH}}-\text{CH}-\text{CH}_2\text{COOR}_4-\underset{R_2}{\text{C}_6\text{H}_4}$$

| ERYTHRO-/THREO | R$_2$ | (F)$_n$ | R$_4$ | RATE | BG | DB | RC | CH | LC | FO | WO | RG | MA | WM | BARLEY LARK | AURA | BONAN | FENM | WHEAT ERA | ANZA |
|---|---|---|---|---|---|---|---|---|---|---|---|---|---|---|---|---|---|---|---|---|
| 57/43 | m-Br | 3,4-diF | CH$_3$ | 1.000 | 9.0 | — | 9.0 | 9.0 | — | 9.0 | 9.0 | — | 7.0 | 9.0 | — | 6.0 | 6.0 | 6.0 | — | 4.0 |
|  |  |  |  | .500 | 9.0 | — | 9.0 | 9.0 | — | 8.0 | 9.0 | — | 6.0 | 9.0 | — | 6.0 | 6.0 | 5.0 | — | 6.0 |
|  |  |  |  | .250 | 7.0 | — | 8.0 | 9.0 | — | 7.0 | 6.0 | — | 3.0 | 9.0 | — | 3.0 | 2.0 | 2.0 | — | 1.0 |
|  |  |  |  | .125 | 0.0 | — | 6.0 | 9.0 | — | 0.0 | 8.0 | — | 0.0 | 9.0 | — | 0.0 | 0.0 | 0.0 | — | 0.0 |
| 60/40 | p-Br | p-F | CH$_3$ | 1.000 | 9.0 | — | 9.0 | 9.0 | — | 9.0 | 9.0 | — | 2.0 | 9.0 | — | 0.0 | 0.0 | 0.0 | — | 4.0 |
|  |  |  |  | .500 | 9.0 | — | 9.0 | 9.0 | — | 9.0 | 6.0 | — | 0.0 | 9.0 | — | 5.0 | 3.0 | 6.0 | — | 5.0 |
|  |  |  |  | .250 | 6.0 | — | 6.0 | 0.0 | — | 9.0 | 0.0 | — | 0.0 | 8.0 | — | 0.0 | 0.0 | 0.0 | — | 0.0 |
|  |  |  |  | .125 | 0.0 | — | 9.0 | 0.0 | — | 9.0 | 0.0 | — | 0.0 | 8.0 | — | 0.0 | 0.0 | 0.0 | — | 0.0 |
| 63/37 | m-F | p-F | benzyl | 1.000 | 6.0 | — | 9.0 | 0.0 | — | 9.0 | 0.0 | — | 0.0 | 8.0 | — | 0.0 | 0.0 | 0.0 | — | 0.0 |
|  |  |  |  | .500 | 0.0 | — | 0.0 | 0.0 | — | 0.0 | 0.0 | — | 0.0 | 8.0 | — | 0.0 | 0.0 | 0.0 | — | 0.0 |
|  |  |  |  | .250 | 0.0 | — | 0.0 | 0.0 | — | 0.0 | 0.0 | — | 0.0 | 4.0 | — | 0.0 | 0.0 | 0.0 | — | 0.0 |
|  |  |  |  | .125 | 0.0 | — | 0.0 | 0.0 | — | 0.0 | 0.0 | — | 0.0 | 3.0 | — | 0.0 | 0.0 | 0.0 | — | 0.0 |

What is claimed is:

1. 4-Cyano-4-(fluorophenyl)-3-substituted-phenyl)-butyric acids, esters and derivatives of formula I below

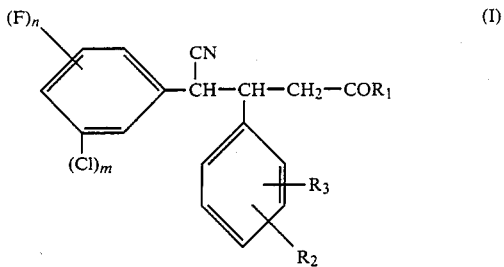

wherein $R_1$ is OH, $OR_4$ or OM; $R_2$ and $R_3$ are each hydrogen, fluorine, chlorine, bromine, iodine, $NO_2$, CN, $C_2$–$C_4$ alkyl, $C_1$–$C_4$ alkoxy, $OCHF_2$, $OCF_2CF_2H$, $OFC_3$, $CF_3$, $S(O)_xCH_3$ or $S(O)_xCF_2R_7$, wherein X is 0, 1 or 2 and $R_7$ is H, F, CHFCl, $CF_2H$ or $CF_3$; provided that $R_2$ and $R_3$ are not both hydrogen; n is an integer of one to three; m is zero or one; $R_4$ is alkyl $C_1$–$C_8$, monohaloalkyl $C_1$–$C_4$, hydroxyalkynyl $C_4$–$C_6$, monohaloalkynyl $C_4$–$C_6$, monohaloalkenyl $C_3$–$C_4$, furfuryl, benzyl or $C_1$–$C_4$ alkoxyethyl; M is an alkali metal, ammonium, $C_1$–$C_8$ mono or dialkylammonium or hydroxyethylammonium; and the stereoisomers thereof.

2. A compound according to claim 1, wherein n is an integer of one or two; $R_2$ and $R_3$ are each hydrogen, bromine, chlorine, fluorine, $CF_3$, $OCH_3$ or $OCHF_2$ with the proviso that $R_2$ and $R_3$ are not both hydrogen.

3. A compound according to claim 2, wherein $R_1$ is $OR_4$.

4. The compound according to claim 2, erythro-/threo-4-cyano-4-cyano-4-(m-fluorophenyl)-3-(p-fluorophenyl)butyric acid or a salt or ester thereof.

5. The compound according to claim 2, erythro-/threo-4-cyano-4-(p-fluorophenyl)-3-(m-fluorophenyl)-butyric acid or a salt or ester thereof.

6. The compound according to claim 2, erythro-/threo-4-cyano-3-(m-chlorophenyl)-4-(m-fluorophenyl)butyric acid or a salt or ester thereof.

7. The compound according to claim 2, erythro-/threo-4-cyano-3-(m-chlorophenyl)-4-(p-fluorophenyl)-butyric acid or a salt or ester thereof.

8. The compound according to claim 2, erythro-/threo-3-(p-chlorophenyl)-4-cyano-4-(3,4-difluorophenyl)butyric acid or a salt or ester thereof.

9. The compound according to claim 2, erythro-/threo-3-(p-chlorophenyl)-4-cyano-4-(m-fluorophenyl)-butyric acid or a salt or ester thereof.

10. The compound according to claim 2, erythro-/threo-3-(m-chlorophenyl)-4-cyano-4-(3,4-difluorophenyl)butyric acid or a salt or ester thereof.

11. The compound according to claim 2, erythro-/threo-4-cyano-4-(3,4-difluorophenyl)-3-(m-fluorophenyl)butyric acid or a salt or ester thereof.

12. The compound according to claim 2, erythro-/threo-4-cyano-3,4-bis(m-fluorophenyl)butyric acid or a salt or ester thereof.

13. The compound according to claim 2, erythro-/threo-3-(3-chloro-4-fluorophenyl)-4-cyano-4-(m-fluorophenyl)butyric acid or a salt or ester thereof.

14. The compound according to claim 2, erythro-/threo-4-cyano-3-4-(m-fluorophenyl)butyric acid or a salt or ester thereof.

15. The compound according to claim 2, erythro-/threo-4-cyano-3-(2,4-difluorophenyl)-4-(m-fluorophenyl)butyric acid or a salt or ester thereof.

16. The compound according to claim 2, erythro-/threo-3-(m-bromophenyl)-4-cyano-4-(3,4-difluorophenyl)butyric acid or a salt or ester thereof.

17. The compound according to claim 2, erythro-/threo-methyl-4-cyano-4-(3,4-difluorophenyl)-3-(p-methoxyphenyl)butyrate.

18. The compound according to claim 2, erythro-/threo-methyl 4-cyano-4-(m-fluorophenyl)-3-(p-methoxyphenyl)butyrate.

19. The compound according to claim 2, erythro-/threo-methyl 4-cyano-4-(p-fluorophenyl)-3-(p-methoxyphenyl)butyrate.

20. The compound according to claim 2, erythro-and threo- methyl 4-cyano-4-(m-fluorophenyl)-3-(m-methoxyphenyl)butyrate.

21. A method for selectively controlling undesirable vegetation in transplanted rice comprising applying to flood water or soil as a preemergence post-transplant or pre-plant incorporated treatment, a herbicidally effective amount of an erythro/threo mixture of a compound of formula I

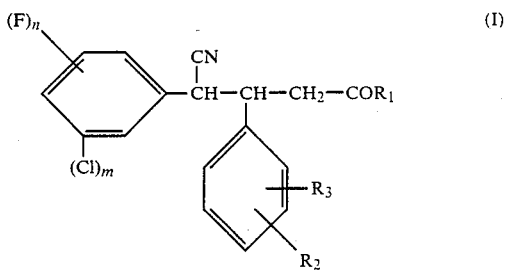

wherein $R_1$ is OH, $OR_4$ or OM, benzyloxy $C_1$–$C_3$ alkyl; $R_2$ is hydrogen, o-fluorine, m-fluorine, m-chlorine, m-bromine or m-$OCH_3$; $R_3$ is hydrogen, p-fluorine, p-$OCH_3$ or p-$CH_3$; provided that $R_2$ and $R_3$ are not both hydrogen; n is an integer of one or two; m is zero or one; $R_4$ is $C_1$–$C_3$ alkyl, $C_1$–$C_4$ alkoxy $C_1$–$C_2$ alkyl, furfuryl or benzyl; M is an alkali metal, $C_1$–$C_3$ mono or dialkylammonium and the stereoisomers thereof.

22. A method according to claim 21, wherein $R_1$ is $OR_4$.

23. A method according to claim 21, wherein the compound is erythro-/ threo-methyl-4-cyano-4-(3,4-difluorophenyl)-3-(p-methoxyphenyl)butyrate.

24. A method according to claim 21, wherein the compound is erythro-/ threo-methyl 4-cyano-4-(m-fluorophenyl)-3-(p-methoxyphenyl)butyrate.

25. A method according to claim 21, wherein the compound is erythro-/ threo-methyl 4-cyano-4-(p-fluorophenyl)-3-(p-methoxyphenyl)butyrate.

26. A method according to claim 21, wherein the compound is erythro-/ and threo- methyl 4-cyano-4-(m-fluorophenyl)-3-(m-methoxyphenyl)butyrate.

27. A method according to claim 21, wherein the compound is erythro-/threo- 4-cyano-4-(m-fluorophenyl)-3-(p-fluorophenyl)butyric acid or a salt or ester thereof.

28. A method according to claim 21, wherein the compound is erythro-/threo- 4-cyano-3-(m-chlorophenyl)-4-(m-fluorophenyl)butyric acid or a salt or ester thereof.

29. A method according to claim 21, wherein the compound is erythro-/ threo- 4-cyano-3-(m-chlorophenyl)-4-(p-fluorophenyl)butyric acid or a salt or ester thereof.

30. A method according to claim 21, wherein the compound is erythro-/threo- 4-cyano-3-(m-fluorophenyl)-4-(p-fluorophenyl)butyric acid or a salt or ester thereof.

31. A method according to claim 21 wherein the compound is erythro-/threo- 3-(m-bromophenyl)-4-cyano-4(3,4-difluorophenyl)butyric acid or a salt or ester thereof.

32. A method for the selective control of undesirable vegetation in transplanted or direct-seeded rice comprising applying to the foliage and stems or to soil containing seeds or other propagating organs of said undesirable vegetation, after the rice has been transplanted or after the direct-seeded rice has emerged from the ground, a herbicidally effective amount of an erythro/threo mixture of a compound having the structure

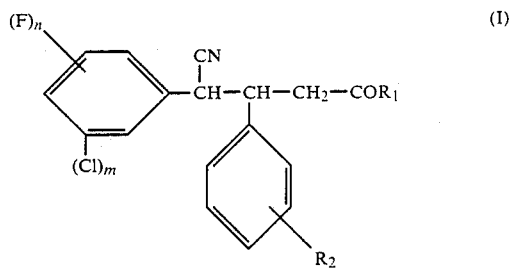

wherein n is an integer of 1 or 2; m is 0 or 1; $R_1$ is OH, $OR_4$ or OM; $R_2$ is o-fluorine, m-fluorine, m-chlorine, m-bromine, m-OCH$_3$, p-fluorine, p-OCH$_3$ or p-CH$_3$; $R_4$ is $C_1$–$C_3$ alkyl, $C_1$–$C_4$ alkoxy $C_1$–$C_2$ alkyl, furfuryl or benzyl; M is an alkali metal, $C_1$–$C_3$ mono- or dialkylammonium; and the stereoisomers thereof.

33. A method according to claim 32, wherein the compound is erythro-/threo- methyl 3-(m-chlorophenyl)-4-cyano-4-(3,4-difluorophenyl)butyrate.

34. A method according to claim 32, wherein the compound is erythro-/threo- methyl 4-cyano-3-(m-fluorophenyl)-4-(p-fluorophenyl)butyrate.

35. A method according to claim 32, wherein the compound is erythro-/threo- 3-(m-bromophenyl)-4-cyano-4(3,4-difluorophenyl)butyric acid or a salt or ester thereof.

36. A method according to claim 32, wherein said compound is erythro-/threo- 4-cyano-4-(m-fluorophenyl)-3-(p-methoxyphenyl)-butyrate.

37. A method for the selective control of undesirable vegetation in wheat and barley comprising applying to the soil containing seeds or other propagating organs of said undesirable vegetation, a herbicidally effective amount of an erythro/threo mixture of a compound having the structure wherein $R_4$ is $C_1$–$C_3$ alkyl, $C_1$–$C_4$ alkoxy $C_1$–$C_2$ alkyl, furfuryl or benzyl.

38. A method according to claim 37, wherein the compound is erythro-/threo- methyl 3-(m-chlorophenyl)-4-cyano-4-(p-fluorophenyl)butyrate.

* * * * *

UNITED STATES PATENT OFFICE
CERTIFICATE OF CORRECTION

Patent No. __4,898,609__     Dated __February 6, 1990__

Inventor(s) __Stephen S. Szucs et al.__

It is certified that error appears in the above-identified patent and that said Letters Patent is hereby corrected as shown below:

Claim 21, line 44, after "metal", -- or -- should be inserted.

Claim 37, line 38, after "having the structure" the following formula should be inserted:

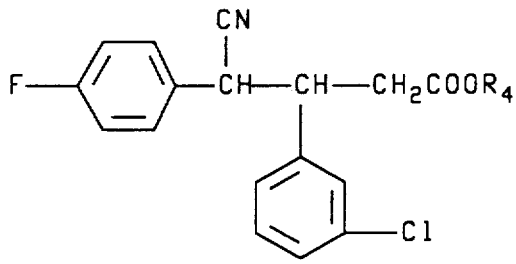

Signed and Sealed this

Eighth Day of October, 1991

Attest:

HARRY F. MANBECK, JR.

*Attesting Officer*      *Commissioner of Patents and Trademarks*